United States Patent [19]

Modolell et al.

[11] Patent Number: 5,266,564
[45] Date of Patent: Nov. 30, 1993

[54] METHOD FOR TREATING CERTAIN AUTOIMMUNE DISEASES

[75] Inventors: Manuel Modolell, Freiburg; Gerhard Munder, Gundelfingen, both of Fed. Rep. of Germany

[73] Assignee: Max-Planck-Gesellschaft Zur Förderung Der Wissenschaften E. V., Göttingen, Fed. Rep. of Germany

[21] Appl. No.: 777,248

[22] PCT Filed: May 31, 1990

[86] PCT No.: PCT/EP90/00870

§ 371 Date: Dec. 23, 1991

§ 102(e) Date: Dec. 23, 1991

[87] PCT Pub. No.: WO90/14829

PCT Pub. Date: Dec. 13, 1990

[30] Foreign Application Priority Data

Jun. 2, 1989 [DE] Fed. Rep. of Germany ....... 3918082

[51] Int. Cl.$^5$ ............................................. A61K 31/685
[52] U.S. Cl. ...................... 514/77; 514/825; 514/885
[58] Field of Search ......................................... 514/77

[56] References Cited

U.S. PATENT DOCUMENTS 4,778,798 10/1988 Munder ................................. 514/77

Primary Examiner—Leonard Schenkman
Attorney, Agent, or Firm—Felfe & Lynch

[57] ABSTRACT

There is described the production of a pharmaceutical composition for the treatment of autoimmune diseases, whereby multiple sclerosis is excluded. As active materials, there are thereby used compounds of the general formula I

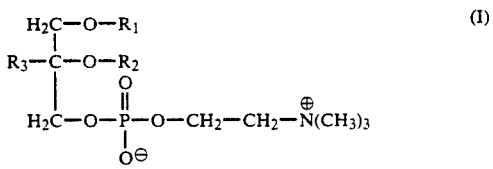

in which $R_1$ represents alkyl with 12 to 18 carbon atoms, $R_2$ alkyl with 1 to 8 carbon atoms and $R_3$ H or alkyl with 1 to 3 carbon atoms.

7 Claims, 18 Drawing Sheets

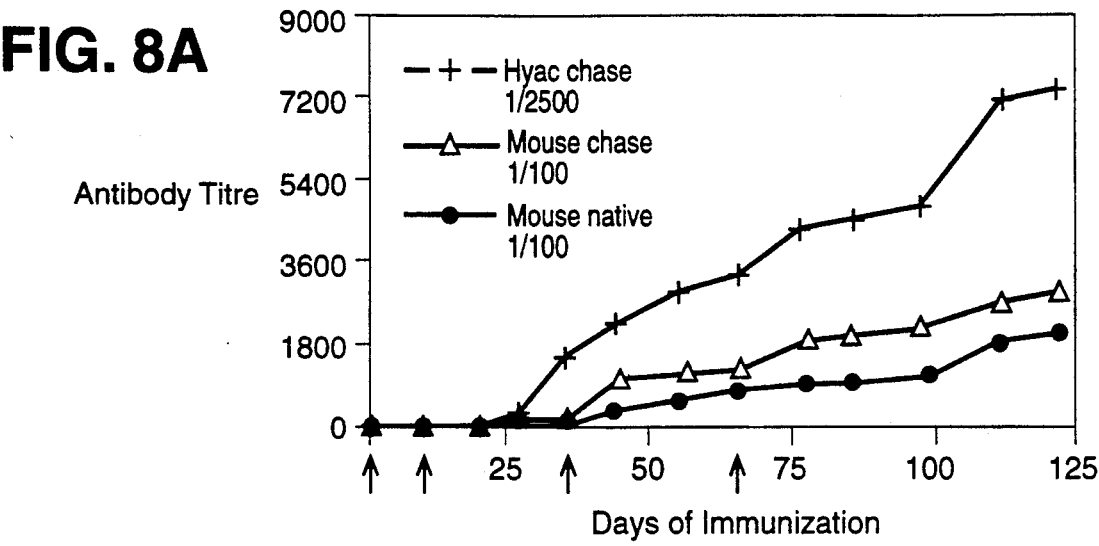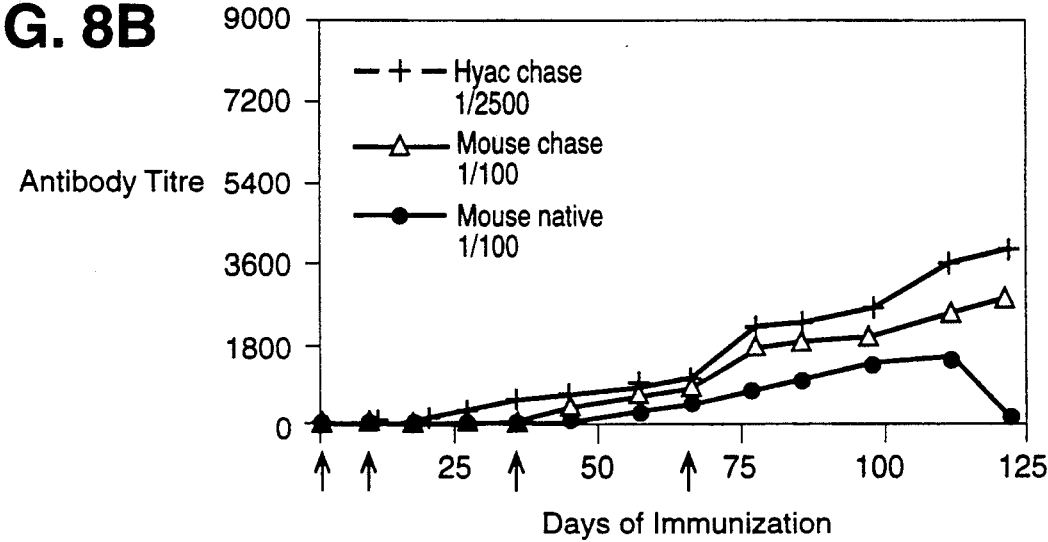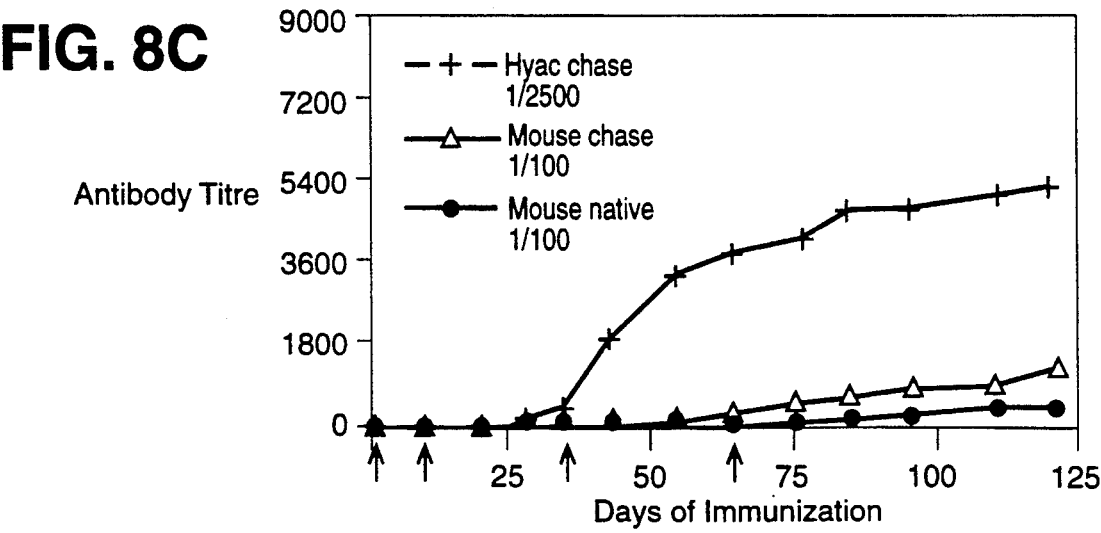

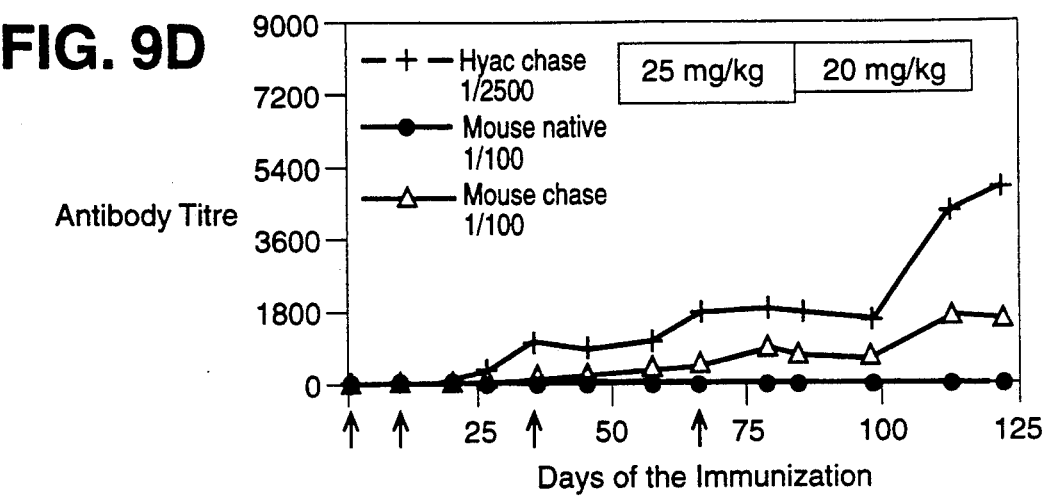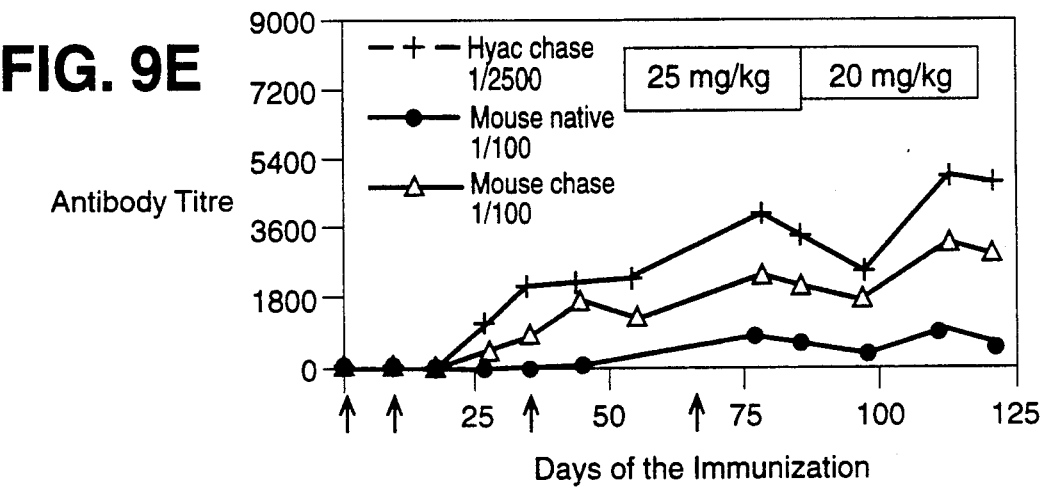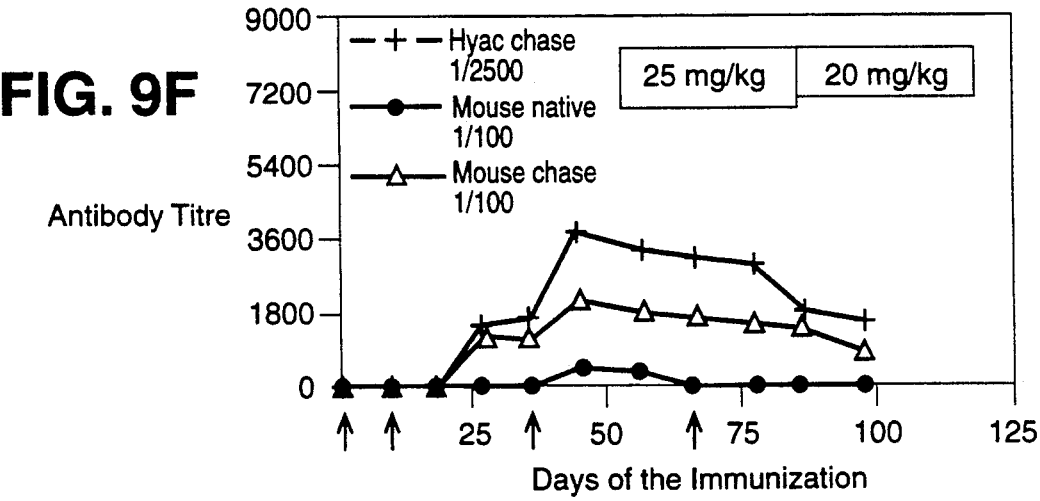

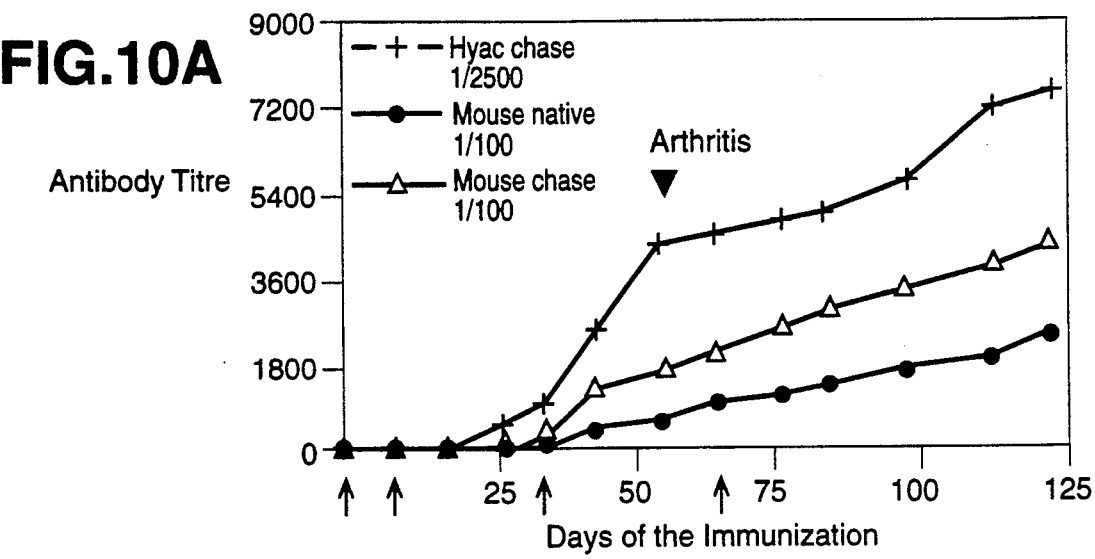
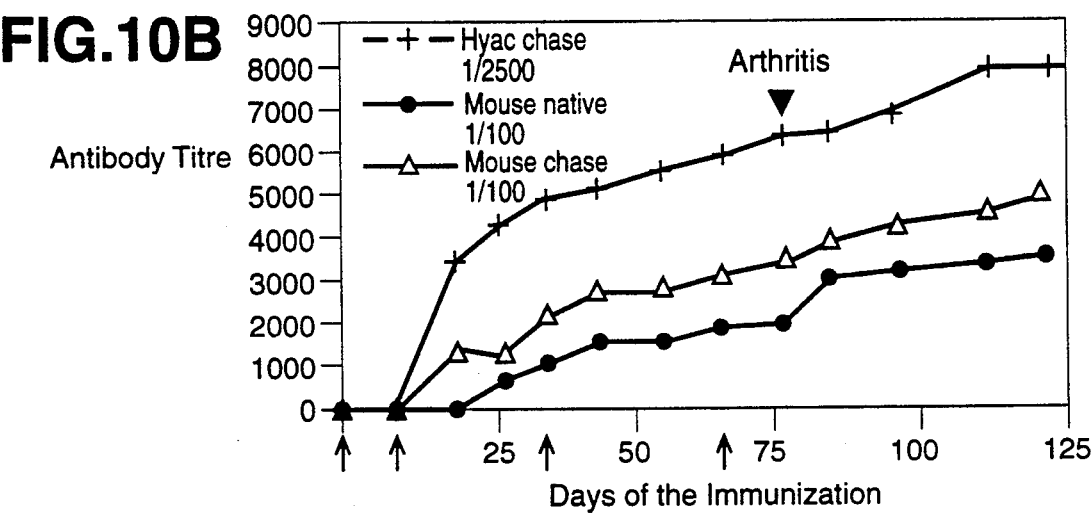
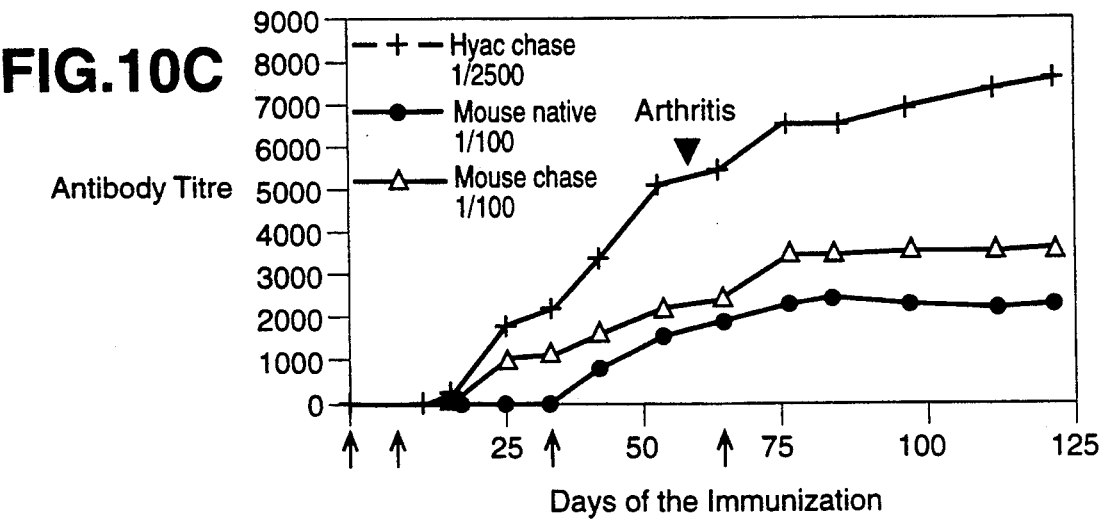

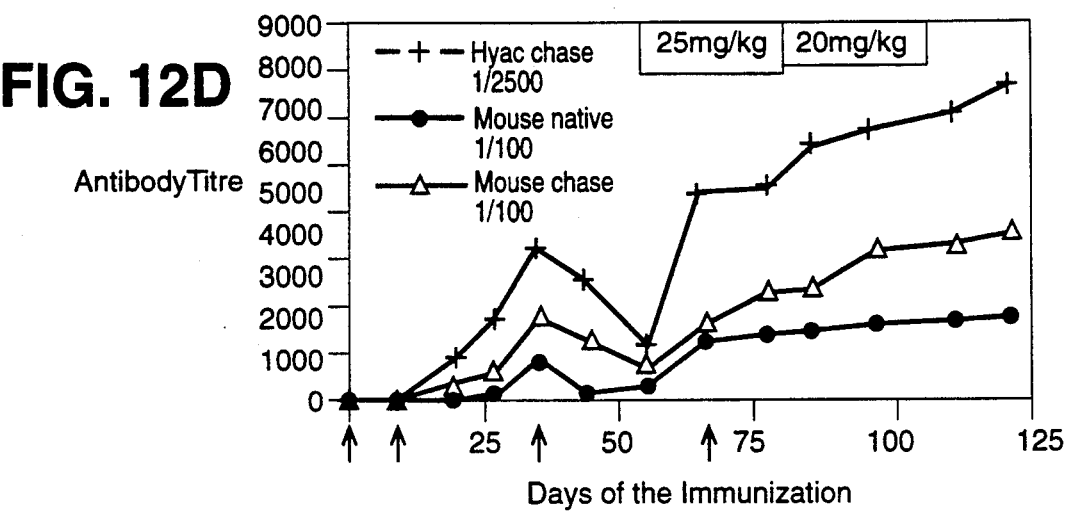
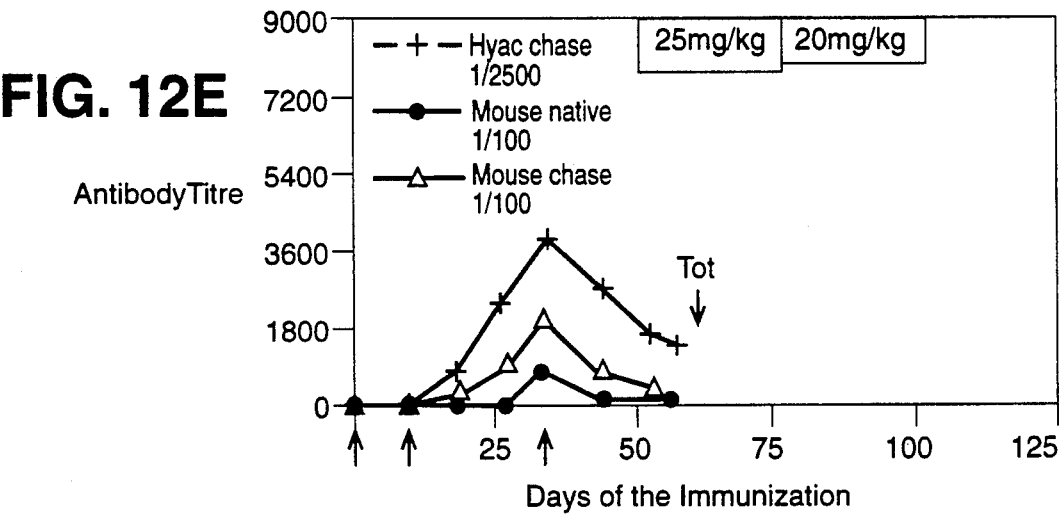
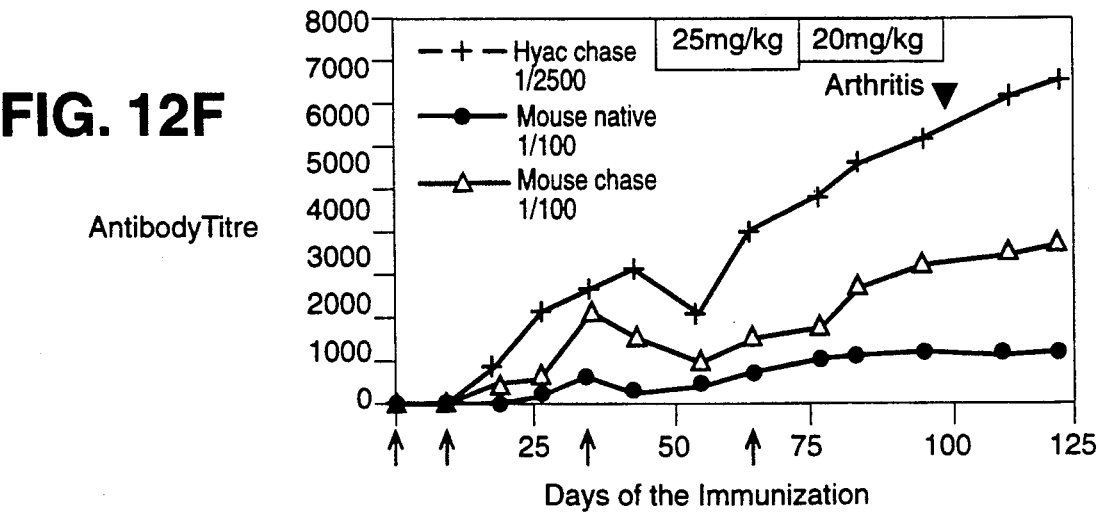

METHOD FOR TREATING CERTAIN AUTOIMMUNE DISEASES

DESCRIPTION

The invention concerns a process for the preparation of a pharmaceutical composition for the treatment of autoimmune diseases with derivatives of lysolecithin.

From DE-OS 20 09 342 and DE-OS 20 09 343 it is already known that synthetic lysolecithin compounds can be used as immunological adjuvants and for the increase of resistance. Furthermore, from DE-OS 26 19 686, it is known that such alkyl-lysophospholipids are effective as antitumorur agents. In addition, it is known that, after administration of lysophosphatides, it results in the formation of activated cells which can increase the resistance of the body against undesired influences. Finally, in U.S. Pat. No. 4,778,788 is described the use of synthetic lysolecithin compounds for the treatment of multiple sclerosis.

In all immunological reactions of the organism, T-lymphocytes play a central part. Their function and their method of working can thereby be divided up into two important working mechanisms, namely:

1. the direct defence against a foreign body, such as bacteria, viruses, parasites and other substances displaying an antigen, whereby the T-lymphocytes participate directly by an effector mechanism, and 2. the regulation of the immune response in order that this does not overshoot.

In both cases, it is characteristic for the manner of working of the T-lymphocytes that these display a high specificity, i.e. that these cells have the property of being able to recognise a single, quite specific antigen. However, before the T-cells show this property, it is necessary that they are first activated from a dormant state, which presupposes a proliferation and a differentiation.

T-lymphocytes can now be divided up into two large sub-groups on the basis of definite membrane structures which are formed by proteins, namely, the CD4+ and the CD8+ T-cells. The CD4 are designated as helper or as inducer T-cells and, inter alia, are responsible for the recognition of foreign proteins and the initiation of defence reactions against antigens. The CD8+ cells, which are designated as suppressor or as cytotoxic T-cells, are responsible, inter alia, for the recognition and the destruction of virus-infected cells.

It has now been shown that, especially in the case of more highly developed species of the animal kingdom, T-cells appear which display auto-reactive properties. This means that such T-lymphocytes are directed against body-inherent structures of the organism and thus are pre-programmed to attack the body's own materials and cells. Normally, these auto-reactive T-cells remain inactive due to the regulating actions of other cells or factors so that an equilibrium for the protection of the organism results. However, if this equilibrium is disturbed, then auto-immune diseases can thereby be induced. This leads to the formation of auto-aggressive cells or auto-antibodies which finally initiate the auto-immune disease. However, hitherto it has not been known which antigens are responsible in the case of humans for the initiation of these symptoms.

Such auto-immune diseases have previously been treated with immune-suppressive substances, such as corticosteroids, cyclophosphamides, cyclosporin A and the like. However, it has been shown that these substances not only inhibit the whole immune system but, in addition, also display considerable side effects, such as a suppression of the bone marrow, carcinogeneity, as well as high toxicity.

The task forming the basis of the invention is to make available a further agent for the treatment of auto-immune diseases which does not display the above-mentioned disadvantages.

R. Andreesen and P. Munder (New Trends Lipid Mediators Res. Basel, Karger, 1988, Vol. 1, pages 16 to 29 and Immunobiol. (1979) 156, 498–508) have already been able to show that alkyl-lysophospholipids are able to inhibit the non-specific proliferation of lymphocytes.

Surprisingly, it has now been found that the proliferation of precisely those specific auto-reactive T-cells which are responsible for the auto-immune reactions can be inhibited by quite specific alkyl-lysophospholipids.

Thus, the subject of the invention is a process for the preparation of a pharmaceutical composition which is characterised in that compounds of the general formula I

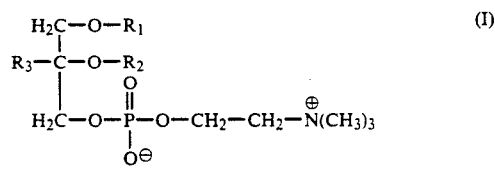

in which $R_1$ represents alkyl with 12 to 18 carbon atoms, $R_2$ alkyl with 1 to 8 carbon atoms and $R_3$ H or alkyl with 1 to 3 carbon atoms, are used.

The alkyl groups $R_1$, $R_2$ and/or $R_3$ can be branched but are preferably straight-chained. In a compound of the general formula I, $R_2$ is preferably an alkyl radical with 1 to 3 carbon atoms and especially methyl and/or $R_3$ is preferably H. Preferred compounds are especially the compound of the formula I with $R_1$ = n-hexadecyl and $R_2$ = methyl radical and $R_3$ = H (compound II) and, in the first place, the compound of the formula I with $R_1$ = n-octadecyl and $R_2$ = methyl and $R_3$ = H (compound III).

The preparation of the compounds of the formula I is known and can take place in one of the ways described in the literature; cf. e.g. D. Arnold et al., Liebigs Ann. Chem. 709, 234–239 (1967); H. U. Weltzien and O. Westphal, Liebigs Ann. Chem., 709, 240–243 (1967).

It has been shown that the pharmaceutical compositions prepared according to the invention are especially well suited for the treatment of rheumatoid arthritis or of ankylosing spondylitis. In the case of this frequently occurring disease, it is a question of a progressive chronic polyarthritis of the general disease which proceeds creepingly or in thrusts. It usually occurs in the 3rd to the 5th decade of life, whereby women are affected about three times more frequently than men. This disease can lead to the most severe crippling.

However, the compositions prepared according to the invention are also suitable for the treatment of Hashimodo thyroiditis, of systemic lupus erythematosus, in the case of Goodpasture's syndrome, pemphigus, in Basedow's disease and myasthenia gravis, as well as against insulin resistance, furthermore, against auto-immune haemolytic anaemia, auto-immune thrombocytopenic purpura, progressive systemic sclerosis, mixed binding tissue diseases, pernicious anaemia, idiopathic Addinson's disease, those cases of infertility in which this is brought about by anti-spermatozoal antibodies, in the case of glomerulo-nephritis, bullous emphidoid, Sjögren's syndrome, in those cases of diabetes mellitus which are brought about by cell-mediated immunity and antibodies against islet cells, in the case of adrenergic medicament resistance, chronic active hepatitis, as well as those failures of the endocrine glands which are brought about by tissue-specific antibodies. Although it is known that, for the causation of an auto-immune disease, a genetic disposition must be present, the actual process which initiates the immunological occurrences is not known. However, it is assumed that viral or bacterial infections thereby play a part.

As already discussed above, ET-18-OCH$_3$ is especially suitable for the treatment of rheumatoid arthritis and ankylosing spondylitis. The action of ET-18-OCH$_3$ was investigated in proteoglycan-induced progressive polyarthritis of Balb/c mice. This animal model shows a strong similarity to rheumatoid arthritis and ankylosing spondylitis in humans, as indicated by clinical investigations, e.g. radiographic analysis and scintigraphic bone investigations and by histopathological studies of joint connections and of the spine (Glant et al., Arthritis rheum. 30 (1987), 201-212; Mikecz et al., Arthritis rheum, 30 (1987), 306-318). The arthritis starts as polyarticular synovitis in bilateral, small peripheral joints and includes a spondylitis which becomes progressive with extensive erosion of cartilage and bone within the joint. The initial, external symptoms of joint inflammation (swelling and redness) appear after the third or fourth intraperitoneal injection of arthritogenic proteoglycans.

The appearance of arthritis in Balb/c mice is dependent upon the appearance not only of cellular but also of humoral response towards cartilage proteoglycans of the host mouse. However, circulating auto-antibodies only appear in hyperimmunised arthritic animals when the cartilage degradation becomes more or less evident. These auto-antibodies react with intact (non-degraded) and chondroitinase ABS-treated cartilage proteoglycans of the mouse and also show a cross-reaction with the immunising proteoglycan (Mikecz et al., Arthritis rheum. 30 (1987), 306-318).

A pretreatment with ET-18-OCH$_3$ protects the animals against the disease or, insofar as the treatment was commenced during the immunisation with arthritogenic proteoglycan, the development of arthritis is considerably delayed. Furthermore, the clinical symptoms, such as e.g. redness and swelling, were less intensive insofar as arthritis had developed in the treated groups. Also fewer peripheral joints were affected than in non-treated animals. The beginning of the treatment with AT-18-OCH$_3$ reduced the level of circulating (auto-)antibodies and suppressed the production of specific antibodies during the whole experimental period. T-lymphocytes from animals which had previously been treated with ET-18-OCH$_3$ did not proliferate in the presence of antigen used for immunisation. The non-specific T-cell stimulation with concavalin A was also significantly suppressed.

It was also found that, with the help of the alkyl-lysophospholipids to be used according to the invention, auto-reactive T-cells can be inhibited, namely, regardless of whether it is thereby a question of CD4+ or CD8+ cells, whereby this inhibition is brought about by a disturbance of the phosphatidylcholine metabolism of the cell. In particular, it is noteworthy that this disturbance is specific only for activated T-cells and non-activated T-cells are thereby not influenced in their synthesis capacity. Since the proliferation of auto-reactive T-cells is an essential prerequisite so that these can act auto-aggressively, an immunosuppression can thus be carried out by means of alkyl-lysophospholipid-induced inhibition.

DETAILED DESCRIPTION OF THE INVENTION

EXAMPLE 1

The auto-reactive CD4+ T-lymphocytes hereby used are responsible for the initiation of experimental auto-immune arthritis (also called adjuvant arthritis) in the rat. They were isolated according to the method of J. Holoshitz et al, Science, Vol. 219 (1983), pages 56 to 58. The proliferation was induced with the antigen PPD (purified protein derivative, purified fraction from tuberculosis bacteria).

Inhibition of the proliferation of CD4+ cells by alkyl-lysophospholipids during the specific rest stimulation in the presence of an antigen:

$1 \times 10^3$ T-lymphocytes (AR 17) are cultured for 48 hours in RPMI 1640+10% foetal calf serum +1 μg of antigen. As antigen presenter cells, $1 \times 10^6$ of irradiated (30 Gy) thymocytes are co-cultured. After this time, per culture 0.5 μCi $^3$H-thymidine is added thereto and, after a further 6 hours culturing, the incorporation of the thymidine into the DNA of the cells is measured.

Figure 1:
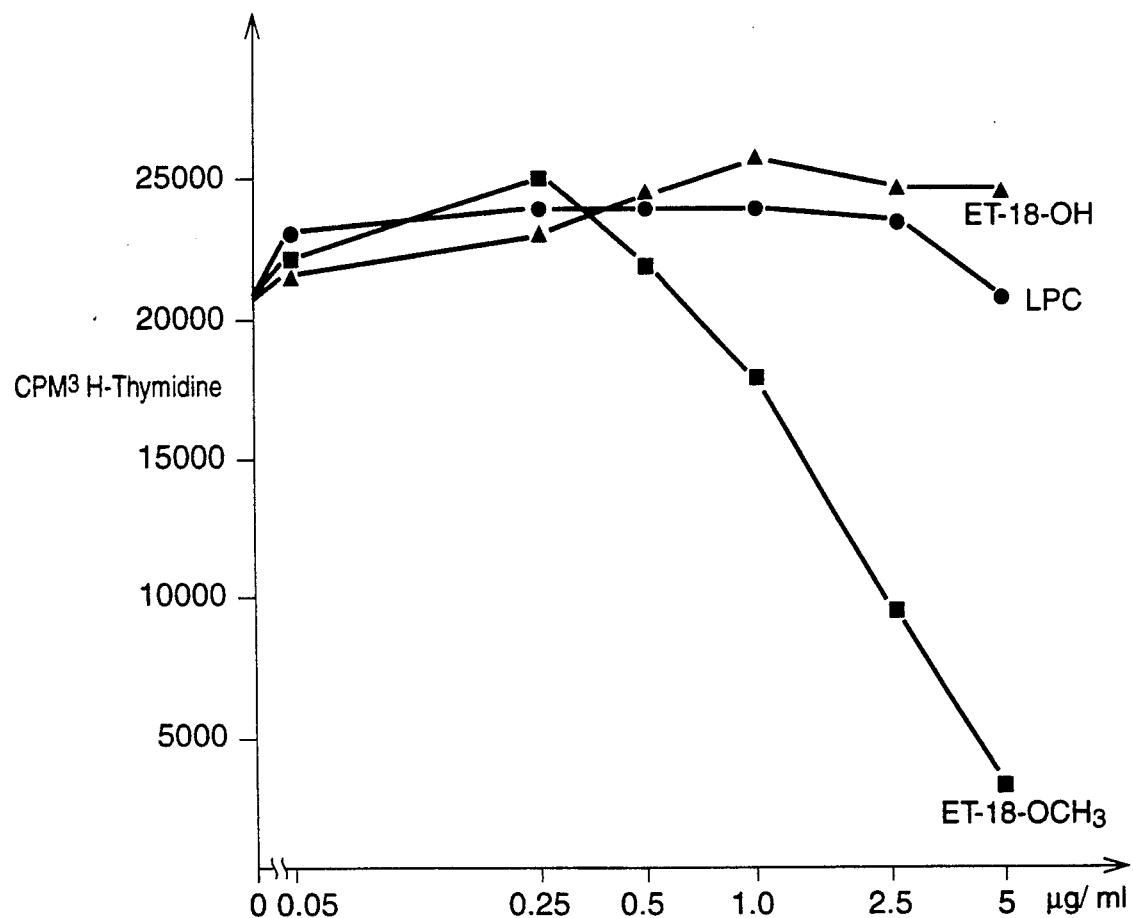
FIG. 1 a graphic representation of the inhibition of the proliferation of auto-reactive CD4+ cells by active materials depending upon their amount.

The result is shown in FIG. 1. From this, it can be seen that the proliferation of the AR 17 cells initiated in this way is inhibited by the substance 1-octadecyl-2-methyl-glycero-3-phosphocholine, in the following called ET-18-OCH$_3$.

EXAMPLE 2

AR 17 cells which have been isolated as described in Example 1 are stimulated to proliferation in culture by the addition of growth factors (IL-2). The inhibition of this proliferation by means of alkyl-lysophospholipids is thereby investigated. The experiment was carried out as follows:

$1 \times 10^3$ T-lymphocytes (AR 17) are cultured for 24 and 48 hours, respectively, in RPMI 1640+10% foetal calf serum+10% culture supernatant from Con A-stimulated spleen cells (IL 2). After this time, 0.5 μCi $^3$H-thymidine is added per culture and, after a further 6 hours culturing, the incorporation of the thymidine in the DNA of the cells is measured.

Figure 2:
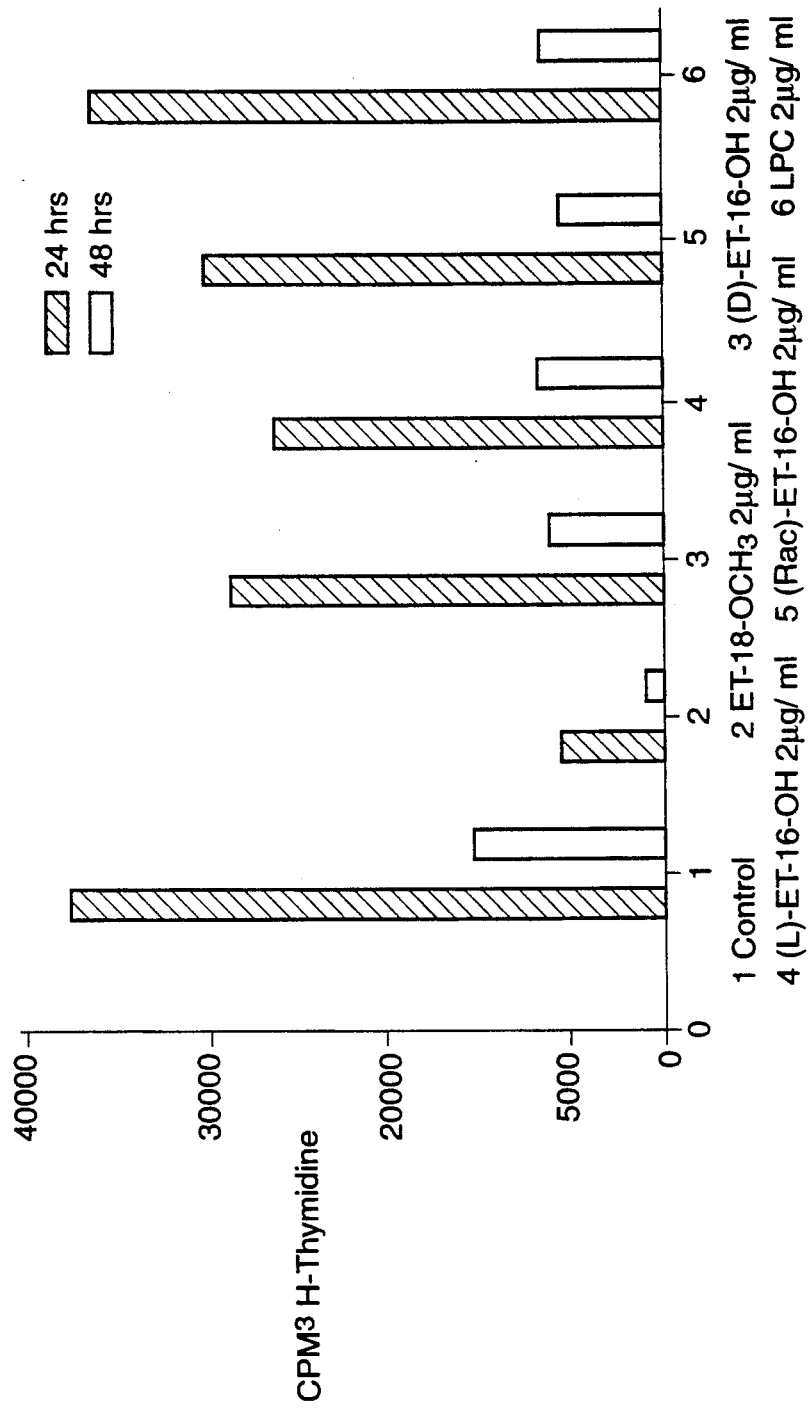
FIG. 2 a representation analogous to FIG. 1 depending upon the experimental period.

The result is illustrated in FIG. 2. It can be seen therefrom that the substance ET-18-OCH$_3$ also shows in this case a marked inhibiting action with regard to the proliferation.

EXAMPLE 3

Figure 3:
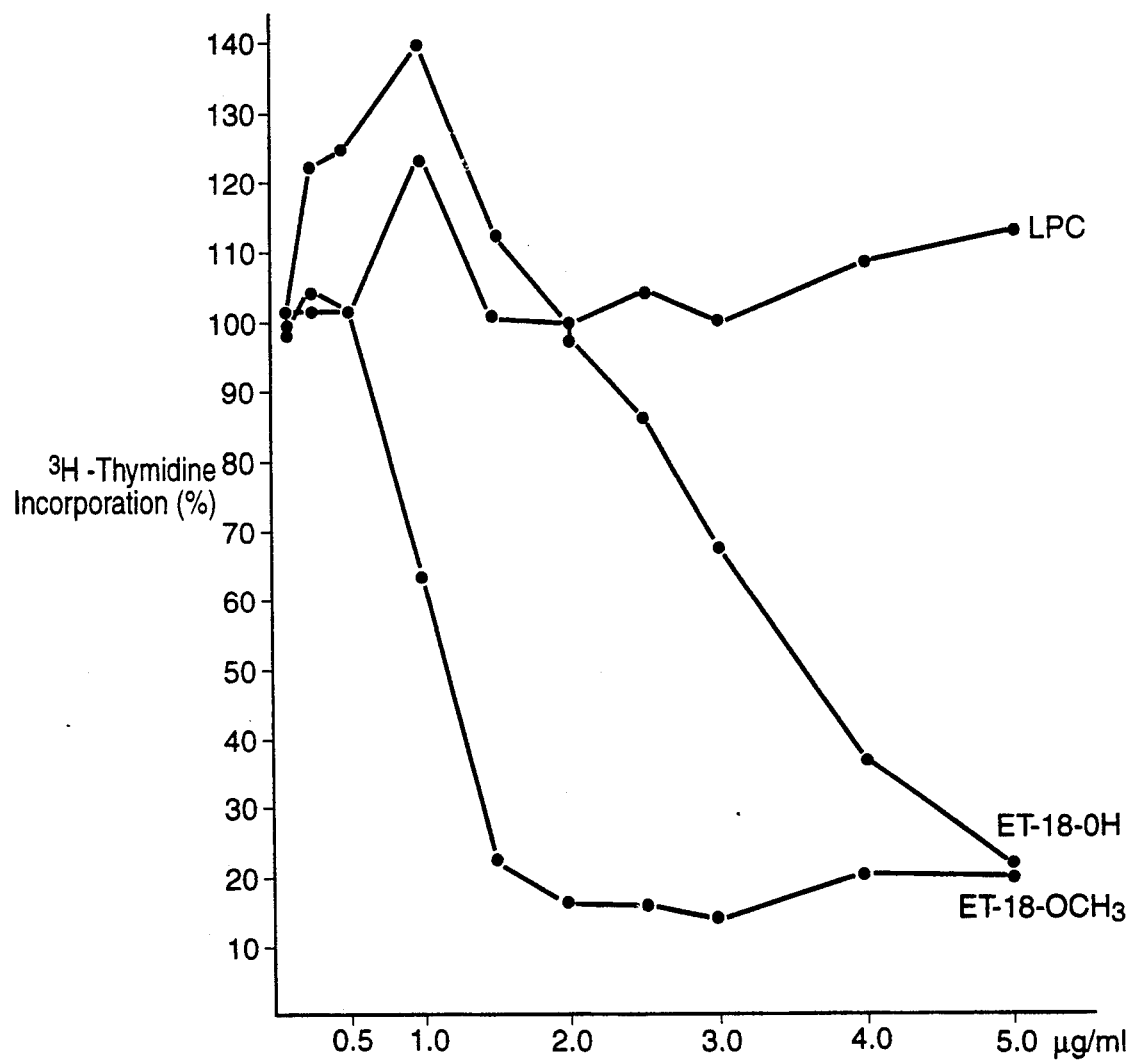
FIG. 3 a representation analogous to FIG. 1 for the proliferation inhibition of CTLL1 cells.

Cytotoxic T-lymphocytes (CTLL1) were isolated as described by M. M. Simon et al., Eur. J. Immunol. (1986), 16, 1269-1276 and the proliferation inhibition of this cell line by alkyl-lysophospholipids investigated. In the case of the cell line hereby used, it is a question of auto-reactive CD8+ T-cells. For the carrying out of the investigation, $1 \times 10^3$ T-lymphocytes (CTLL-1) were cultured for 48 hours in RPMI 1640+10% foetal calf serum+10% culture supernatant from Con-A stimulated spleen cells (IL2). After this time, 0.5 μCi $^3$H-thymidine is added thereto per culture and, after culturing for a further 6 hours, the incorporation of the thymidine in the DNA of the cells is measured. The results are shown in FIG. 3 in percentage values with regard to the control measurements. As can be seen from this Figure, not only ET-18-OH but also ET-18-OCH$_3$ show a marked inhibition of the proliferation.

EXAMPLE 4

Figure 4:
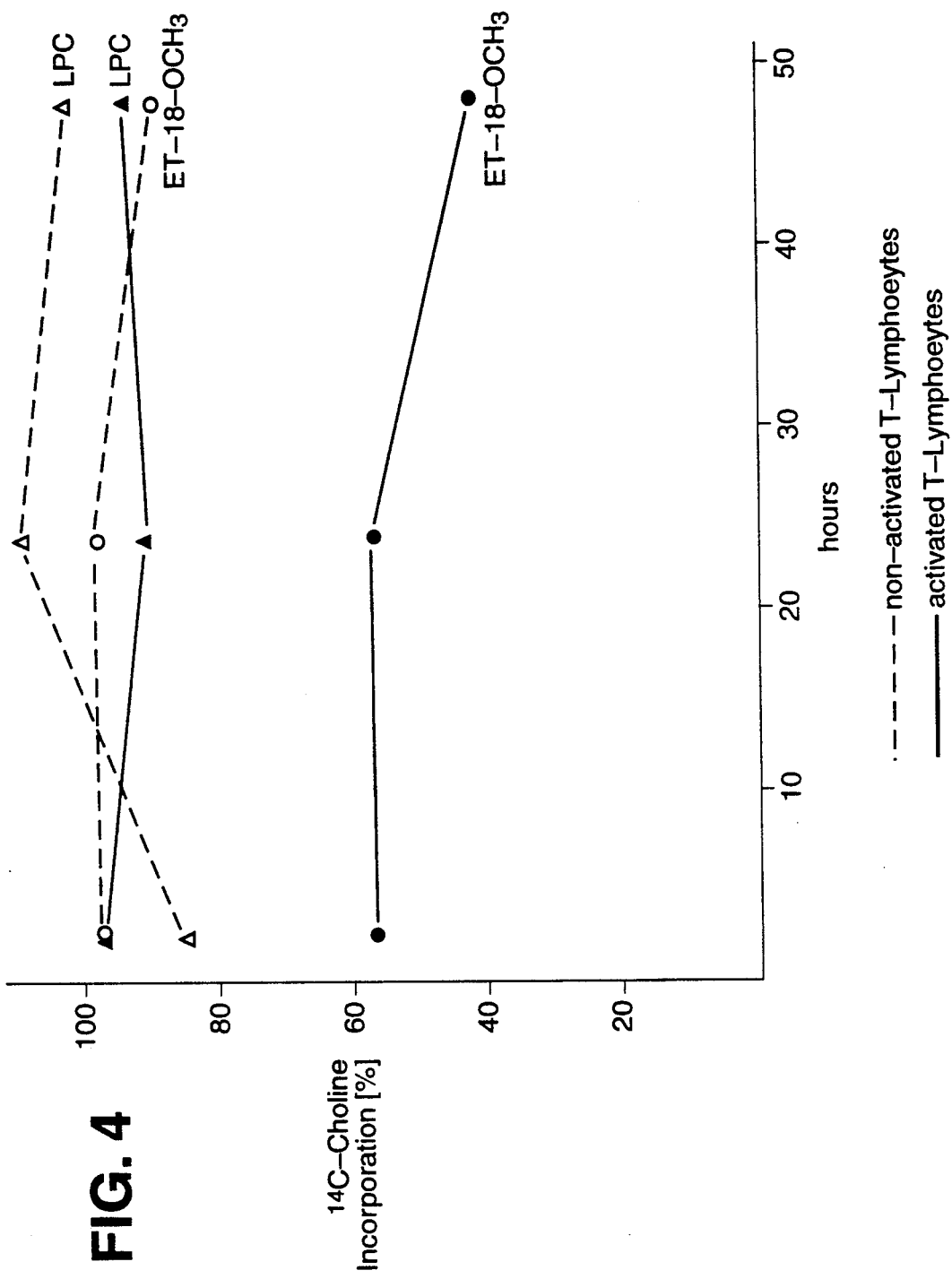
FIG. 4 a graphic representation of the de novo synthesis capacity of T-lymphocytes (choline incorporation) in the presence of ET-18-OCH$_3$ depending upon the activation state of the cells.

The incorporation of radioactive-labelled choline into phosphatidylcholine was investigated and, in this way, the de novo synthesis capacity of the cells determined. $1 \times 10^6$ T-lymphocytes were thereby cultured for the given period of time in choline-free DMEM (Dulbecco's modification of Eagle's medium)+10% foetal calf serum+10% culture supernatant from Con A-stimulated spleen cells (IL 2)+0.5 Ci $^{14}$C-choline. The phospholipids of the cells are extracted, separated by thin layer chromatography and the radioactivity of the phosphatidylcholine bands is measured with a TLC scanner. The results are shown in FIG. 4. The broken line thereby shows the choline incorporation into un-stimulated T-cells and the unbroken line the incorporation into stimulated CD4+ T-cells (AR 17). The individual results are given in percentage, referred to the control values. It is thereby shown that, surprisingly, ET-18-OCH$_3$ only inhibits the synthesis of activated auto-reactive AR 17 T-cells, whereas the non-activated T-lymphocytes, which do not participate in the auto-immune reaction, remain uninfluenced by this substance in their synthesis capacity.

EXAMPLE 5

The fatty acid composition of phosphatidylcholine is continuously renewed by the action of phospholipase A as deacylating enzyme and of acyl transferase as reacylating enzyme. In order to detect this metabolism, the T-cells were previously incubated with $^{14}$C-oleic acid so that the phosphatidylcholine was radioactively labelled by incorporation of this fatty acid.

Figure 5:
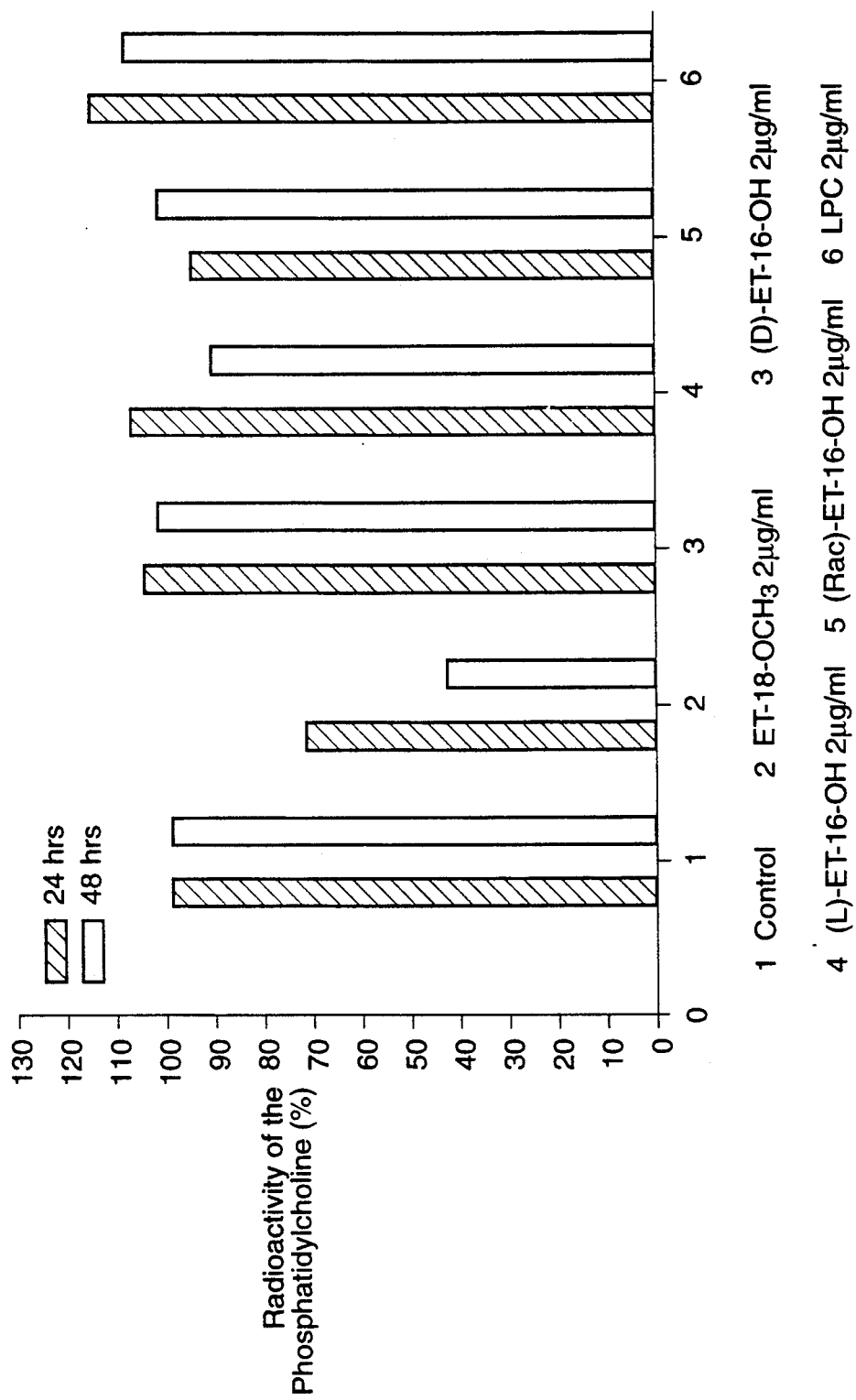
FIG. 5 a graphic representation of the degradation of phosphatidylcholine by AR17 T-cells in the presence of ET-18-OCH$_3$.
Figure 6:
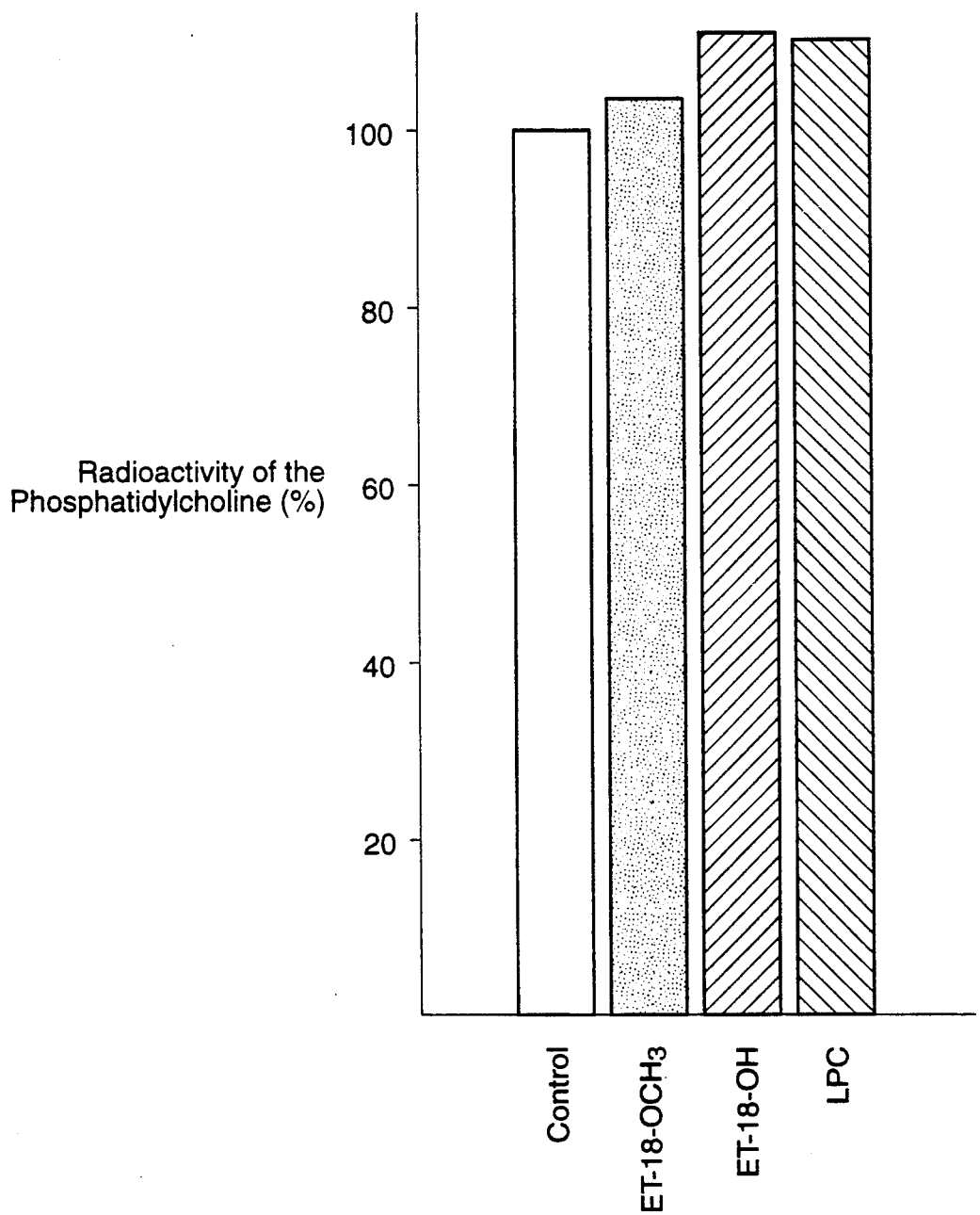
FIG. 6 a representation analogous to FIG. 5 for non-activated T-cells.

There was now determined the breakdown of phosphatidylcholine in AR 17 T-cells by the addition of various alkyl lysophospholipids. $1 \times 10^6$ T-lymphocytes were thereby cultured in DMEM+1% foetal calf serum+0.1 μCi $^{14}$C-oleic acid for 4 hours. Thereafter, the labelled cells are further cultured with various alkyl lysophospholipids for 24 and 48 hours, respectively, in DMEM+10% foetal calf serum+10% culture supernatant from Con A-stimulated spleen cells (IL 2). The phospholipids of the cells are extracted, separated by thin layer chromatography and the radioactivity of the phosphatidylcholine bands measured with a TLC scanner. In FIG. 5, the results are shown as percentage, referred to the control values. It can be seen therefrom that the cells which have been incubated with ET-18-OCH$_3$ show a high loss of radioactivity, which means a loss of phosphatidylcholine. As is to be seen from FIG. 6, in contradistinction thereto, non-activated T-cells show no action with regard to an incubation with this substance.

EXAMPLE 6

Action of ET-18-OCH$_3$ on the formation of proteoglycan-induced arthritis

Induction of primary arthritis

Proteoglycan from human chondrophytes cleaved with chondroitinase ABC (corresponding to proteoglycan from immature human articular cartilage (HYAC)) was used for the immunisation of 5 to 6 weeks old female Balb/c mice (Charles River Colony, Montreal, Quebec) as already described (Gland et al., Arthritis rheum 30 (1987), 201-212; Mikecz et al., Arthritis rheum. 30 (1987), 306-318). 100 μg of proteoglycan protein of chondroitinase ABC-cleaved HYAC were injected intraperitoneally in 100 μl of phosphate-buffered saline (PBS), pH 7.2 and with Freund's complete adjuvant, in a 1:1 emulsion with PBS. They were again injected three times with the antigen in Freund's incomplete adjuvant on days 9, 35 and 65. Control female Balb/c mice were immunised with non-arthritogenic (bovine articular) proteoglycan (BAC-PG) or with phosphate-buffered saline (PBS) and adjuvant without proteoglycan antigens.

Groups of this experiment are listed in Table I. Originally, 10 animals in group 9 were pretreated with ET-18-OCH$_3$ and subsequently treated with arthritogenic proteoglycan from human chronrophytes, as in the case of groups 6 (immunised, non-treated), 7 (immunised, non-treated but fed with milk daily) and 8 (immunised and treated with ET-18-OCH$_3$ dissolved in milk).

TABLE I
EXPERIMENTAL GROUPS, IMMUNIZATION AND TREATMENTS OF BALB/c MICE

| Group No: | Number of animals | Immunization with | Immune status: antibodies to HYAC-PG | Immune status: antibodies to Mouse-PG | Clinical status | Treatment with ET-18-OCH3 |
|---|---|---|---|---|---|---|
| 1 | 5 | none | — | — | non-arthritic | — |
| 2 | 5 | saline | — | — | non-arthritic | solvent |
| 3 | 5 | saline | — | — | non-arthritic | + |
| 4 | 5 | BAC-PG | + | ± | non-arthritic | solvent |
| 5 | 6 | BAC-PG | + | ± | non-arthritic | + |
| 6 | 5 | HYAC-PG | + | + | arthritic | — |
| 7 | 6 | HYAC-PG | + | + | arthritic | solvent |
| 8 | 6 | HYAC-PG | + | + | late and weak arthritic | + |
| 9 | 10 | HYAC-PG | + | + | non arthritic | pretreated |

Animals were injected with an emulsion of saline and Freund's adjuvants or immunized with proteoglycan antigens in Freund's adjuvants.
Abbreviations:
HYAC-PG = proteolycan from human chondrophyte (osteophyte cartilage)
BAC-PG = proteoglycan from bovine articular cartilage
saline = phosphate buffered saline, pH 7.4 (0.01M $PO_4$ in 0.14 M NaCl)
solvent = milk (which was otherwise used to dissolve ET-18-OCH3.

Animals from two groups (No. 4 and No. 5) were immunised with BAC-PG and treated or non-treated with ET-18-OCH3, whereas 15 mice in three further groups served as negative controls (Table I). I$_n$ each group were 5 to 10 female Balb/c mice 5–6 weeks old at the beginning of the experiment. The animals were treated with ET-18-OCH3 dissolved in milk (low fat milk) by oesophageal probe (oral administration of the drugs) for 12 weeks (25 mg/kg for 5 to 6 weeks and 20 mg/kg for 6 weeks). The dose of ET-18-OCH3 was reduced from 25 mg/kg to 20 mg/kg since the physical condition of the treated Balb/c mice became continuously worse from the second week of the treatment and 4' animals of group 9 and two animals of group 8 were lost in weeks 3 to 4 of the treatment with ET-18-OCH3. The animals (apart from group 9, see above) were treated with ET-18-OCH3 from week 5 to week 17 of the experiment and then sacrificed.

Each statement of time given in this report (see FIGS. 8 to 10, 12 and 13) begins on the day of the first injection.

SERUM SAMPLES, ANTIBODY TESTS

Serum samples were collected from the retro-orbital venous plexus on days 1, 9, 19, 27, 35, 44, 55, 65, 77, 85, 97 and 112. The samples were stored at −20° C. until the final bleeding on day 122, whereby the antibody titres in 13 serum samples of each animal were simultaneously determined and compared.

The antibodies in the sera were determined by a radioimmune test in solution, whereby $^{125}$I-labelled cartilage from human neonates (chondroitinase ABC-treated (=chase)) and from the mouse (intact (=native) add and chondroitinase ABC-treated) were used. Each serum was tested at a dilution of 1:100, 1:500 and 1:2500 and sometimes at 1:12,500 as already described (Mikecz et al., supra; Glant et al., Biochem. J. 234, 31–41). For this purpose, 100 µl of diluted serum were incubated with $^{125}$I-labelled proteoglycan (10,000 c.p.m. in 50 µl) for 4 hours at room temperature. After the incubation, 25 µl of protein A-carrying Staphylococcus aureus (5% weight/volume) were added, incubated for 30 minutes at 37° C. and washed twice. The radioactivity of the residues was determined in a Backman gamma counter.

TESTS FOR LYMPHOCYTE REACTIVITY

The response of splenocytes to concavalin A (Con A as mouse T-cell mitogen) and cartilage proteoglycan antigens (BAC-PG and HYAC-PG) were determined as already described (Mikecz et al., supra). The stimulation of lymphocytes was expressed as an index which is a ratio of the cpm of antigen- or mitogen-stimulated cultures to the cpm of non-stimulated cultures.

ASSESSMENT OF THE ARTHRITIS

The limb measurements of all mice (arthritic and non-arthritic, immunised and non-immunised) were examined daily in order to demonstrate clinical arthritic changes which were documented as already described (Glant et al., Arthritis Rheum 30 (1987), 201–212). Swelling and redness, as the first clinical symptoms of the appearance of arthritis, and the thickness (diameter) of knee, ankle, wrist and the dorso-volar thickness of the hand were recorded.

CLINICAL AND HISTOLOGICAL INVESTIGATIONS

The counts of the red and white blood cells (erythrocytes and leukocytes), as well as the haemogram of the white blood cells, were determined before the experiment, at week 11 (after 6 weeks treatment) and at the end of the experiment (on day 122).

The limbs, tails, lumbar spine and organs were fixed, the bones were decalcified and prepared for section for histological studies.

RESULTS

Groups 1, 2 and 3 (non-immunised, non-arthritic control animals)

These Balb/c mice (in each case 5 in a group) have not been immunised with proteoglycan antigen but the animals of groups 2 and 3 were injected with an emulsion of physiological saline and Freund's adjuvant (Table I). None of these animals produced antibodies to any cartilage component, including proteoglycans and collagent type II and they did not develop arthritis.

Figure 7:
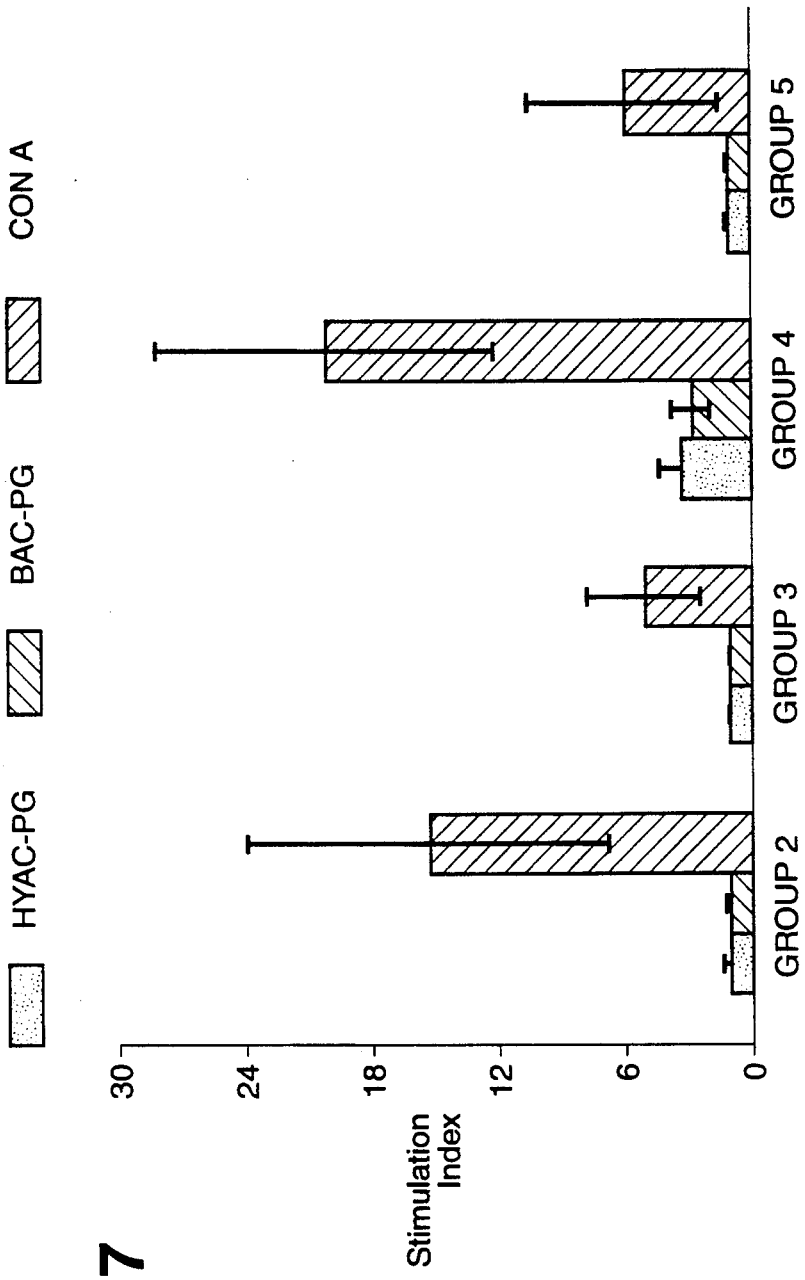
FIG. 7 a graphic representation of a lymphocyte stimulation test of immunised Balb/c mice of the groups 2 to 5.

The treated animals in group 3 lost body weight and became slightly anaemic (Table 2) (probably due to the frequent blood sampling), whereas no other clinical symptoms or laboratory parameters changed. Only the lymphocyte stimulation with a T-cell mitogen (con A) was decreased significantly (FIG. 7).

TABLE II

COMPARISON OF BODY-WEIGHT, RED CELL NUMBER IN PERIPHERAL BLOOD AND THE INTER-MALLEOLAR DIAMETERS OF ARTHRITIC AND NON-ARTHRITIC BALB/c MICE ON DAYS 1, 71 AND 122 OF THE EXPERIMENT

| Groups | Day of experiment | Body weight (g) | Red cell number ($\times 10^6$/ul) | Inter-malleolar diameter (mm) |
|---|---|---|---|---|
| 2 | 1 | 19.9 ± 2.7 | 9.13 ± 0.62 | 3.16 ± 0.05 |
|   | 71 | 27.2 ± 1.2 | 8.78 ± 0.49 | 3.14 ± 0.05 |
|   | 122 | 27.4 ± 1.6 | 8.02 ± 0.32 | 3.16 ± 0.07 |
| 3 | 1 | 19.6 ± 2.6 | 9.26 ± 0.51 | 3.13 ± 0.13 |
|   | 71 | 24.2 ± 1.4 | 8.04 ± 0.66 | 3.18 ± 0.08 |
|   | 122 | 24.8 ± 0.9 | 6.43 ± 0.60 | 3.16 ± 0.13 |
| 6–7 | 1 | 19.2 ± 2.7 | 9.18 ± 0.26 | 3.17 ± 0.05 |
|   | 71 | 25.2 ± 3.4 | 8.75 ± 0.19 | 3.64 ± 0.12 |
|   | 122 | 24.9 ± 3.9 | 7.92 ± 0.28 | 3.71 ± 0.24 |
| 8 | 1 | 19.2 ± 1.6 | 8.72 ± 0.24 | 3.17 ± 0.04 |
|   | 71 | 22.6 ± 3.1 | 6.25 ± 0.21 | 3.19 ± 0.08 |
|   | 122 | 21.4 ± 4.3 | 5.38 ± 0.32 | 3.32 ± 0.18 |
| 9 | 1 | 17.8 ± 2.9 | 8.22 ± 0.24 | 3.16 ± 0.04 |
|   | 71 | 19.1 ± 1.9 | 7.95 ± 0.19 | 3.16 ± 0.05 |
|   | 122 | 23.4 ± 3.7 | 6.42 ± 0.73 | 3.17 ± 0.07 |

Groups 4 and 5 (animals immunised with non-arthritogenic proteoglycans)

The animals of groups 4 and 5 were immunised with proteoglycans of bovine articular cartilage (BAC) but only group 5 was treated with ET-18-OCH$_3$ (Table I). As expected, none of these animals of groups 4 and 5 developed arthritis.

Figure 8D:
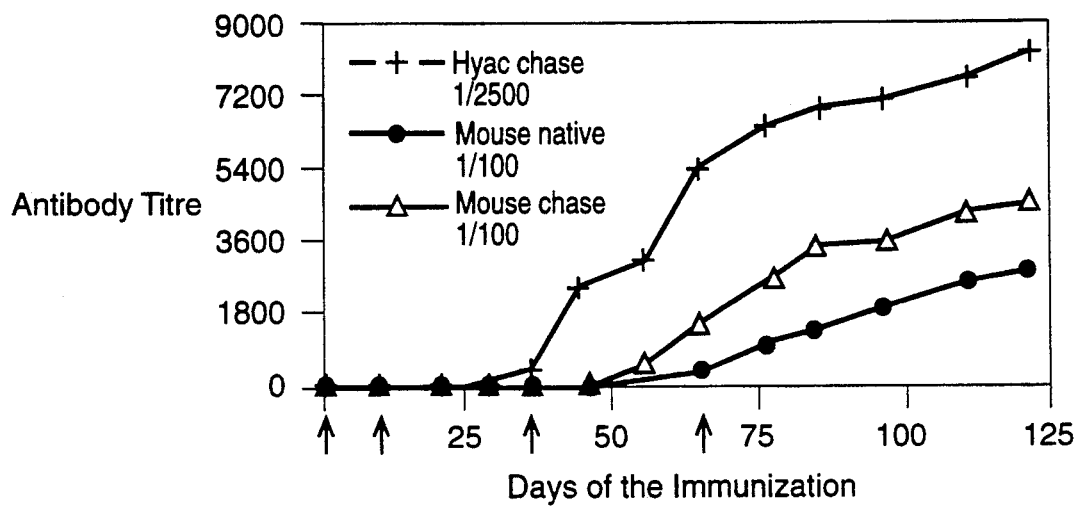
FIG. 8 a graphic representation of the antibody level in animals of group 4 which had been immunised with proteoglycans of bovine articular cartilage (BAC-PG)
Figure 8E:
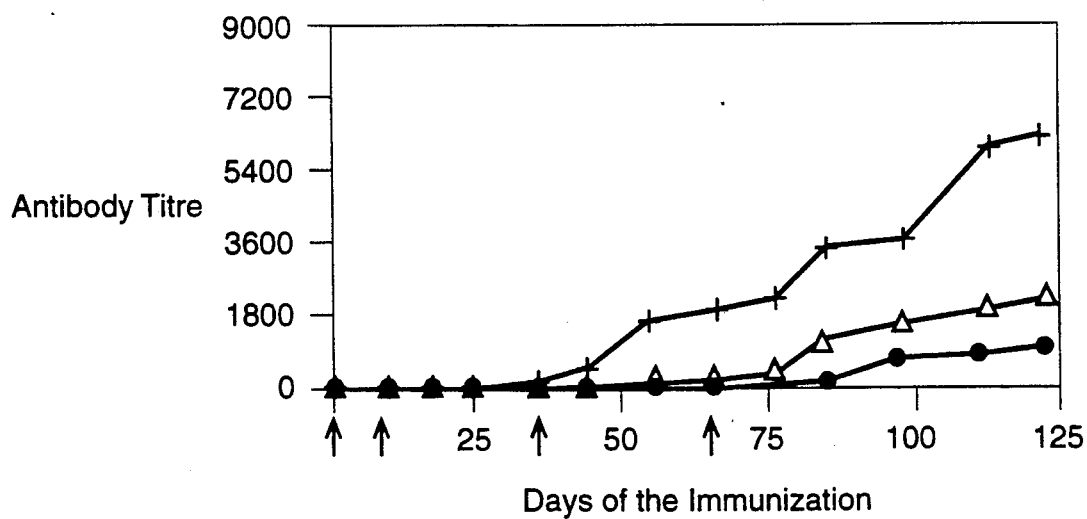

The animals of groups 4 showed a "normal" antibody production towards immunising bovine articular proteoglycan and a continuously increased antibody titre towards cross-reacting but non-arthritogenic epitopes on human (HYAC) and mouse proteoglycans (FIG. 8). Although antibodies against cartilage proteoglycans of the mouse have been found, it is assumed that these cross-reacting antibodies do no participate in the development of the disease. The lymphocyte response, expressed as stimulation index (Mikecz et al., supra) was significantly increased in the presence not only of BAC but also of HYAC proteoglycans (FIG. 7).

Figure 9A:
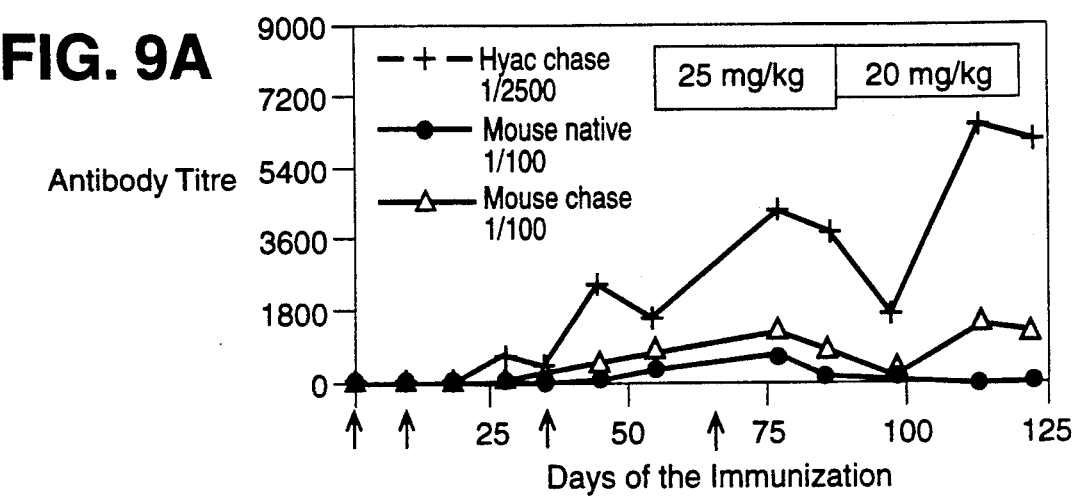
FIG. 9 a representation of the action of ET-18-OCH$_3$ on the antibody level in the serum of Balb/c mice of group 5 which had been immunised with proteoglycans of bovine articular cartilage (BAC-PG)
Figure 9B:
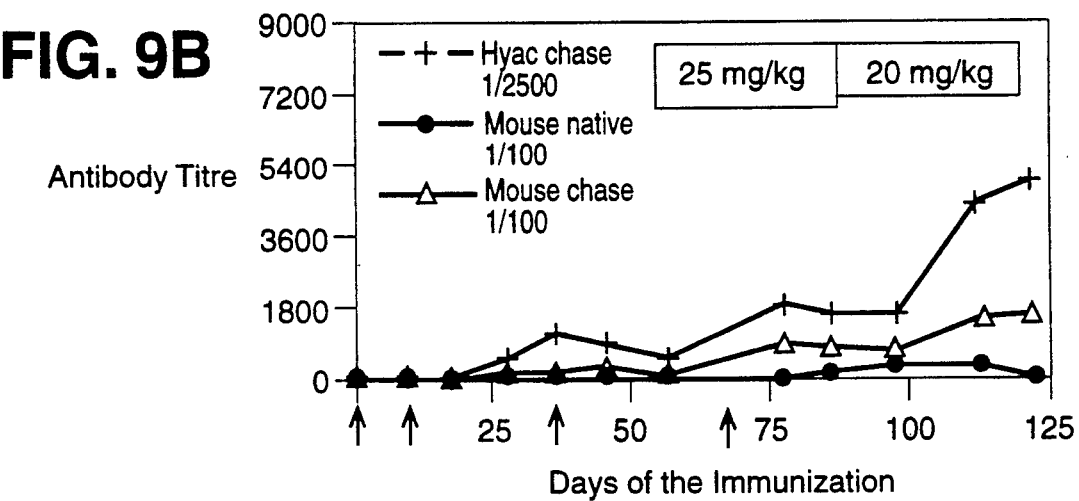
Figure 9C:
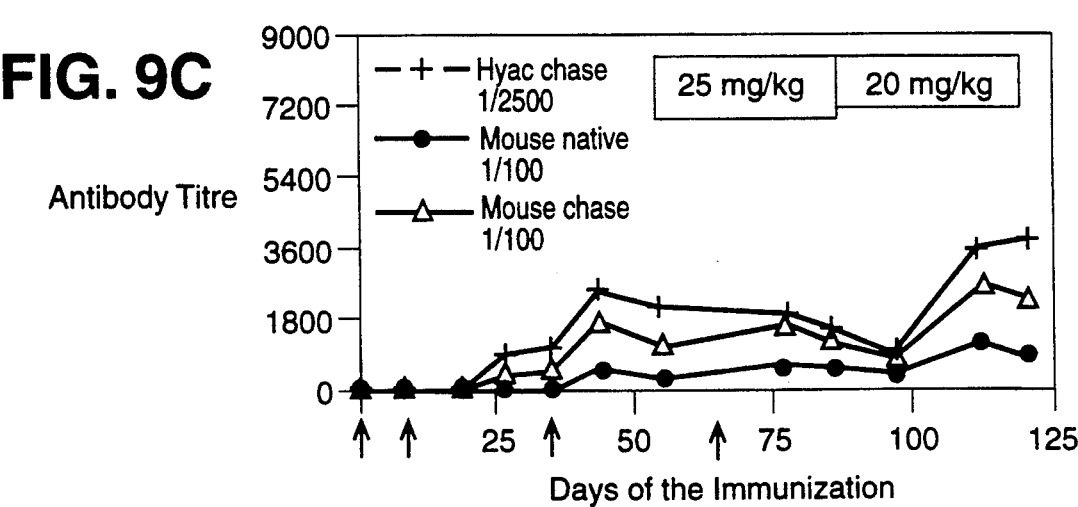
Figure 10D:
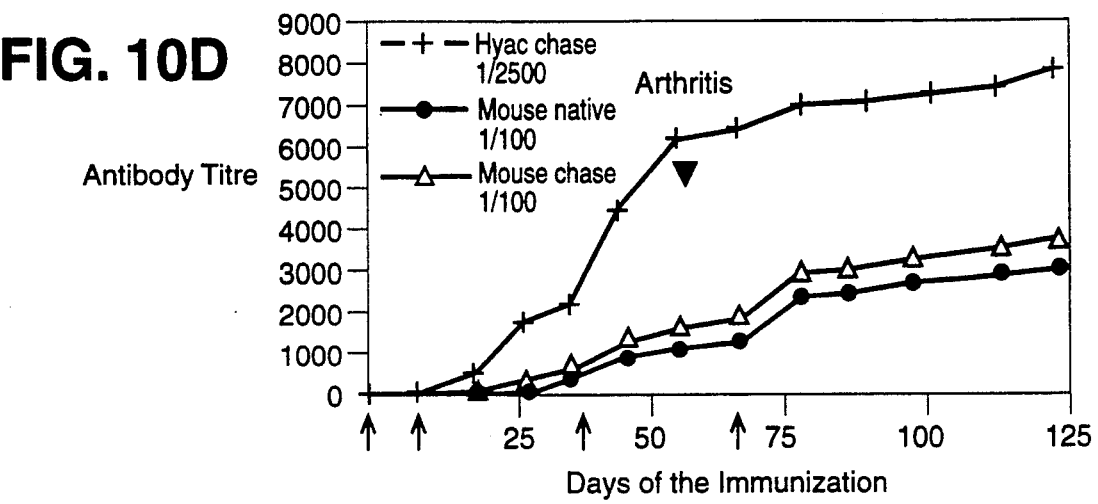
FIG. 10 a graphic representation of the antibody level in the serum of animals of group 7 which had been immunised with proteoglycans of human osteophyte cartilage (HYAC-PG)
Figure 10E:
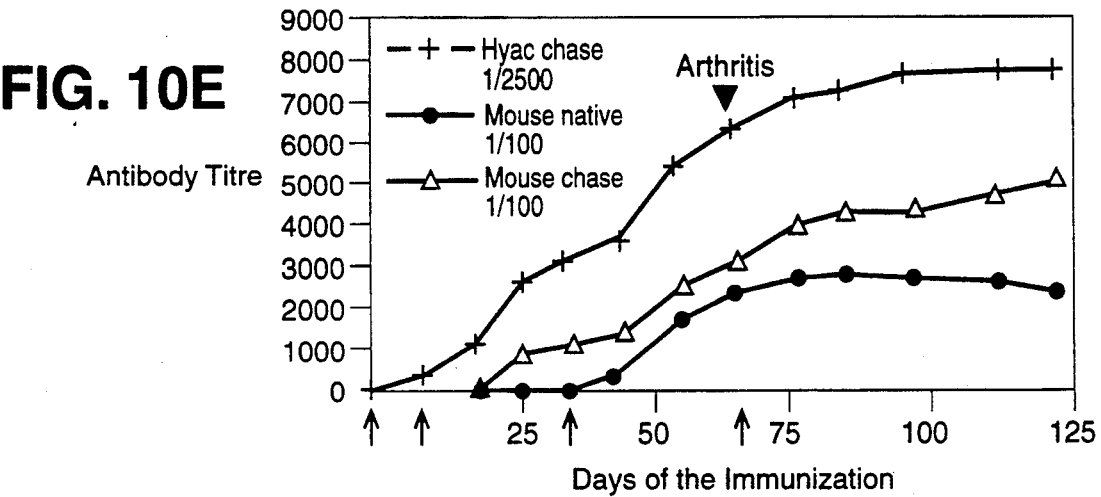
Figure 10F:
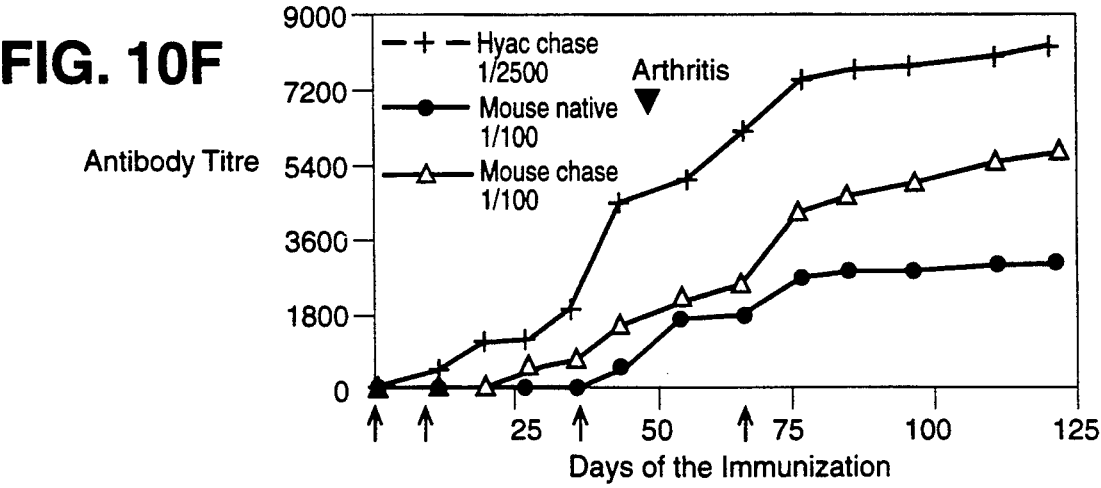

The animals of group 5 (Table I) produced a lower antibody level not only towards bovine (data not shown) or human proteoglycans and auto-antibodies against cartilage proteoglycans of the mouse were scarcely found even at a 1:100 serum dilution (FIG. 9). The level of circulating antibodies was reduced after a two week treatment with ET-18-OCH$_3$, whereby this effect at a dosage of 25 mg/kg per day was more characteristic than a dosage of 20 mg/kg per day. However, the antibody production increased continuously during the whole period of treatment (FIG. 9). The lymphocyte stimulation not only with proteoglycan antigens or Con A was clearly suppressed even after ending of the oral treatment with ET-18-OCH$_3$ (FIG. 7).

Groups 6 and 7 (animals immunised with HYAC but non-treated with ET-18-OCH$_3$)

Animals of these two groups (Table I) were immunised and tested as already described (Gland et al., Arthritis Rheum. 30 (1987), 201–212; Mikecz et al., Arthritis Rheum. 30 (1987), 306–318). No difference was found between animals of group 6 and 7, whereby the latter group was fed daily with milk without ET-18-OCH$_3$ during the whole period of treatment. The animals produced antibodies against HYAC proteoglycans and a high level of autoantibodies against cartilage proteoglycans of the mouse. All animals developed arthritis after the third or immediately after the fourth intraperitaneal injection of HYAC proteoglycan (FIG. 10), which was progressive and led to deformaties and to ankylosis of peripheral joints as already described (Gland et al., Arthritis rheum. 30 (1987), 201–212). The in vitro proliferation of splenocytes of these arthritic animals are summarised in FIG. 11, which shows the characteristic stimulation of lymphocytes in the presence of proteoglycan antigens and Con A.

Group 8 (animals immunised with HYAC and treated with ET-18-OCH$_3$)

Figure 12A:
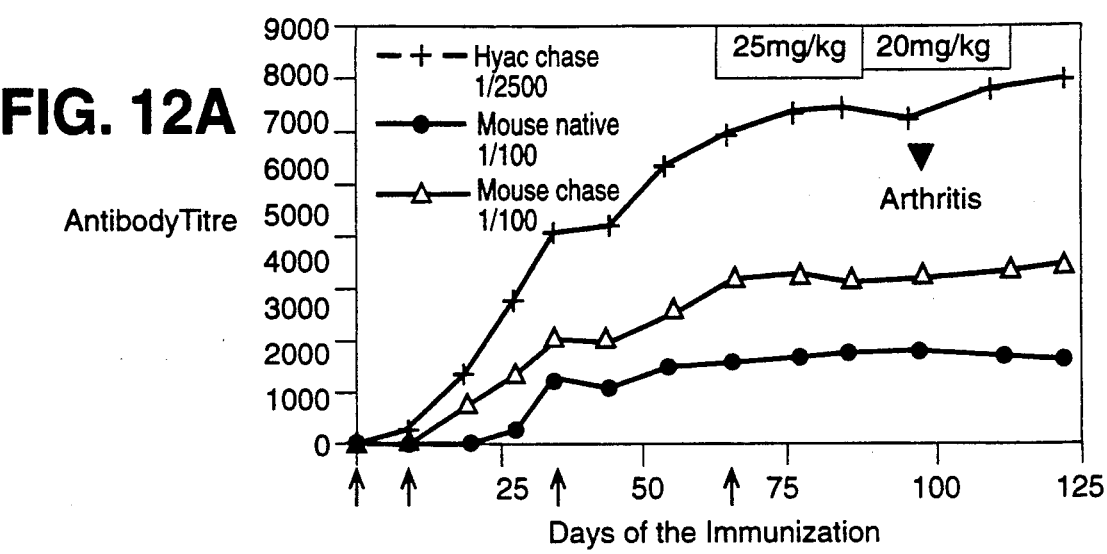
FIG. 12 a graphic representation of the action of ET-18-OCH$_3$ on the antibody level in the serum of Balb/c mice of group 8 which had been immunised with HYAC-PG.
Figure 12B:
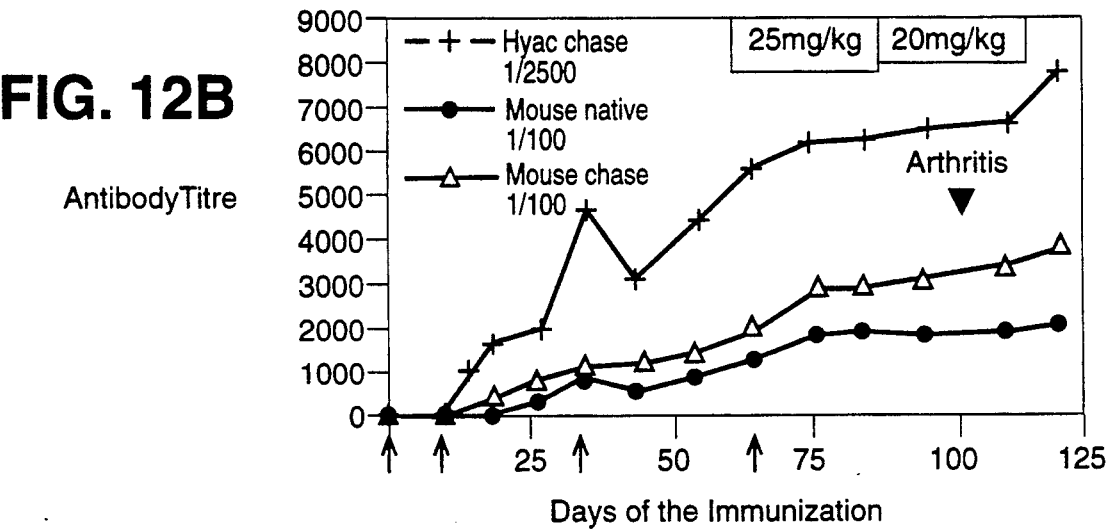
Figure 12C:
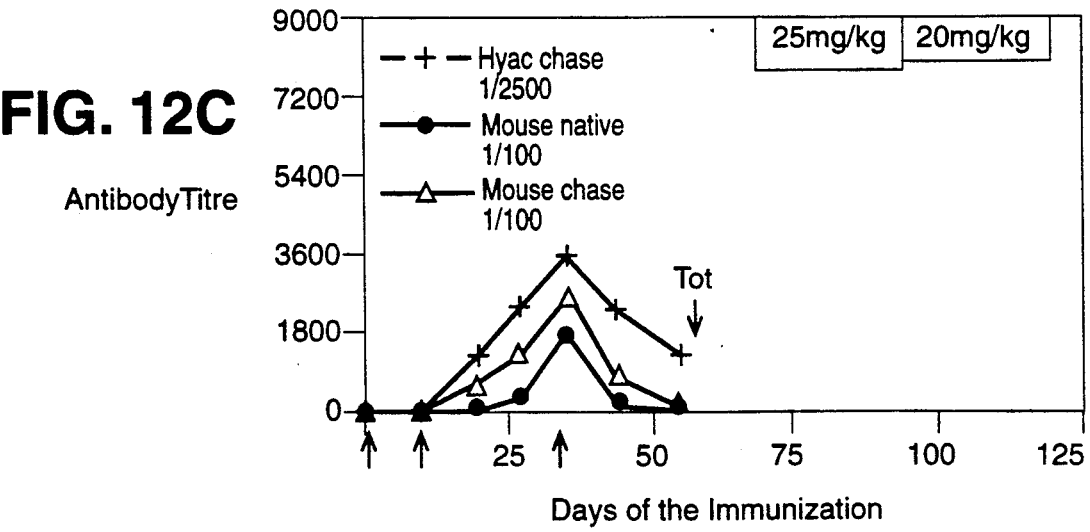
Figure 13A:
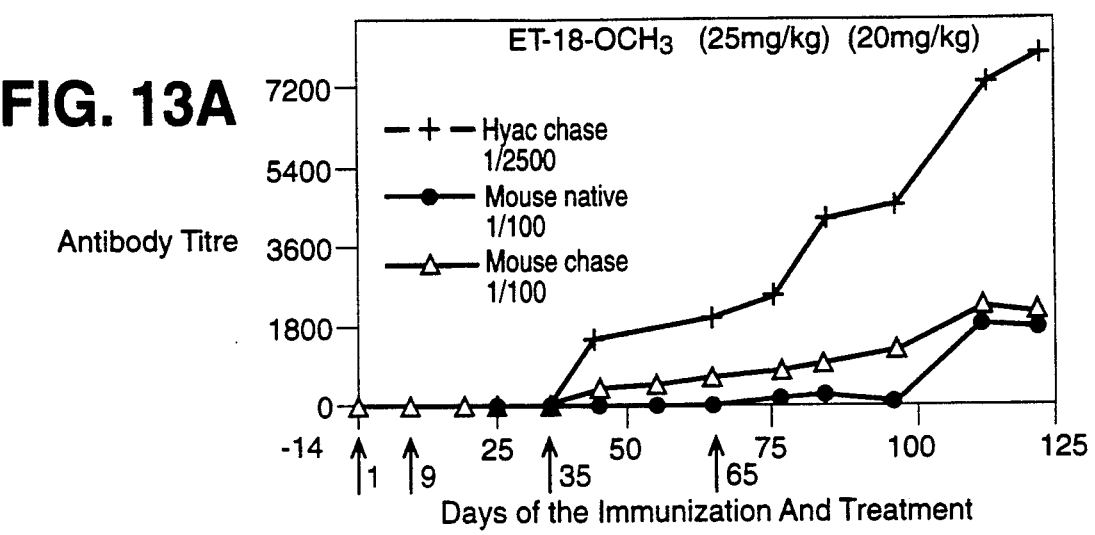
FIG. 13 a graphic representation of the antibody level in the serum of Balb/c mice which had been pretreated with ET-18-OCH$_3$ and subsequently immunised with HYAC-PG.
Figure 13B:
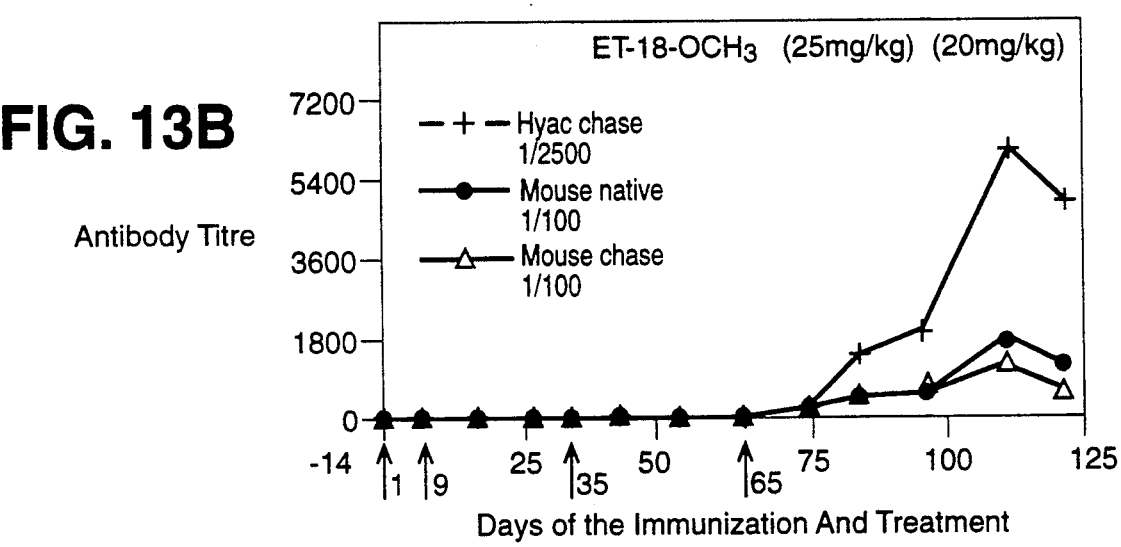
Figure 13C:
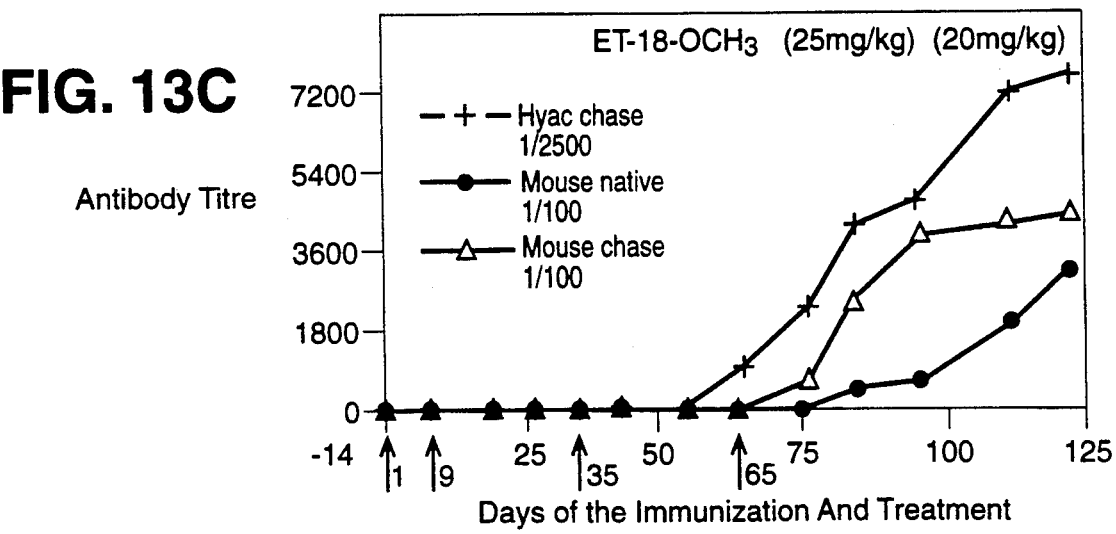
Figure 13D:
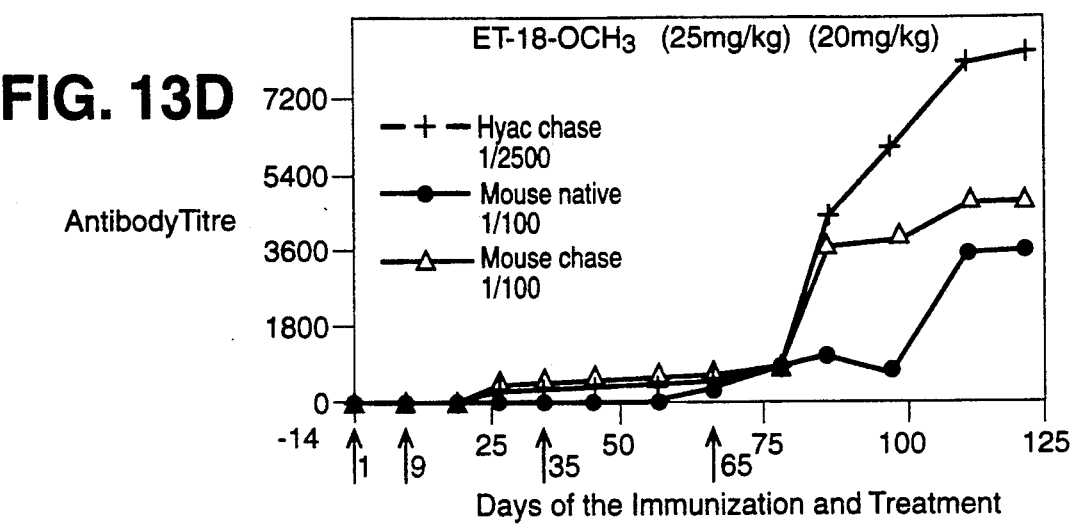
Figure 13E:
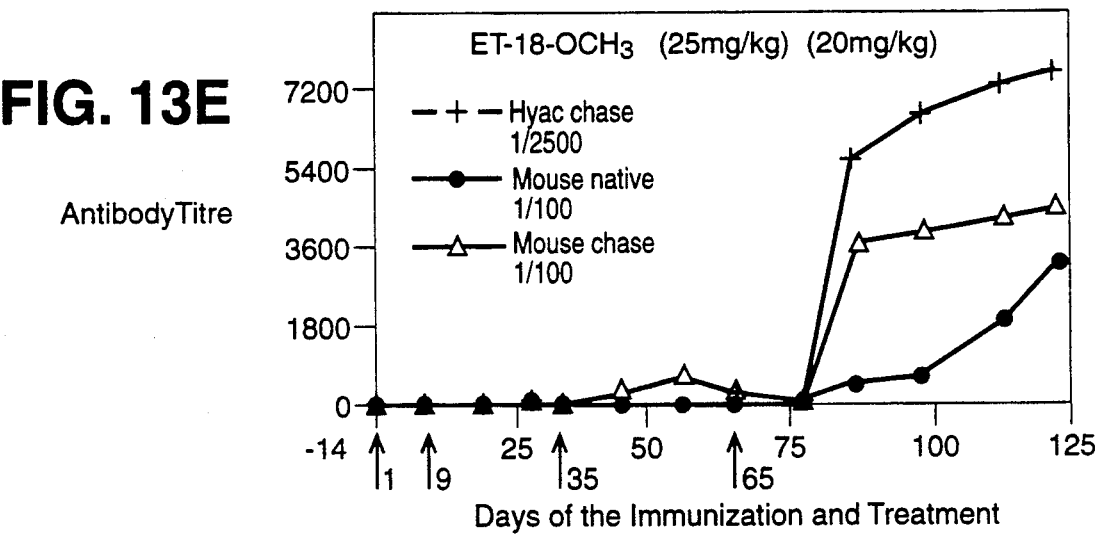
Figure 13F:
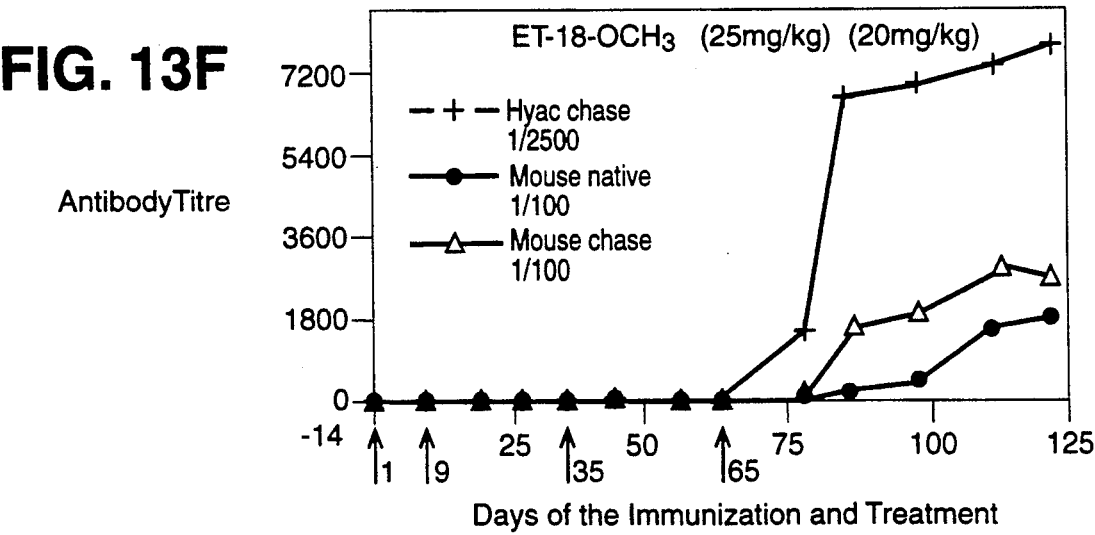

6 animals of group 8 were immunised with proteoglycans of HYAC (like the animals in groups 6 and 7) but they were treated with ET-18-OCH$_3$ for 12 weeks. Since the animals were in a physically poor condition and two animals died in the third and fifth weeks of treatment, the ET-18-OCH$_3$ dose had to be reduced from 25 mg/kg per day to 20 mg/kg per day from the sixth week of the treatment (FIG. 12). This reduction of the dose helped insofar as the animals which were previously in bad physical condition recovered. 3 of 4 animals of this group developed arthritis but the appearance of arthritis occurred significantly later and all clinical symptoms (e.g. redness and swelling expressed as intermalleolar diameter) were milder and the number of joints involved was less than in groups 4 and 5 (Table 2).

Animals in this group (No. 8) and all treated groups (Nos. 3, 5 and 9) were slightly more anaemic than animals in other groups (Nos. 2, 4, 6 and 7) which had not been treated with ET-18-OCH$_3$ (Table II). This can be either the consequence of a direct action of ET-18-OCH$_3$ on bone marrow cells or an indirect action of the general weaker physical condition which is expressed e.g. by the body weight in Table II. However, slight anaemia was observed in all mice as a consequence of frequent blood sampling. Other laboratory parameters, such as e.g. proteinuria (not found), the number and the ratio of the white cells, showed no significant difference between treated and non-treated animals.

Figure 11:
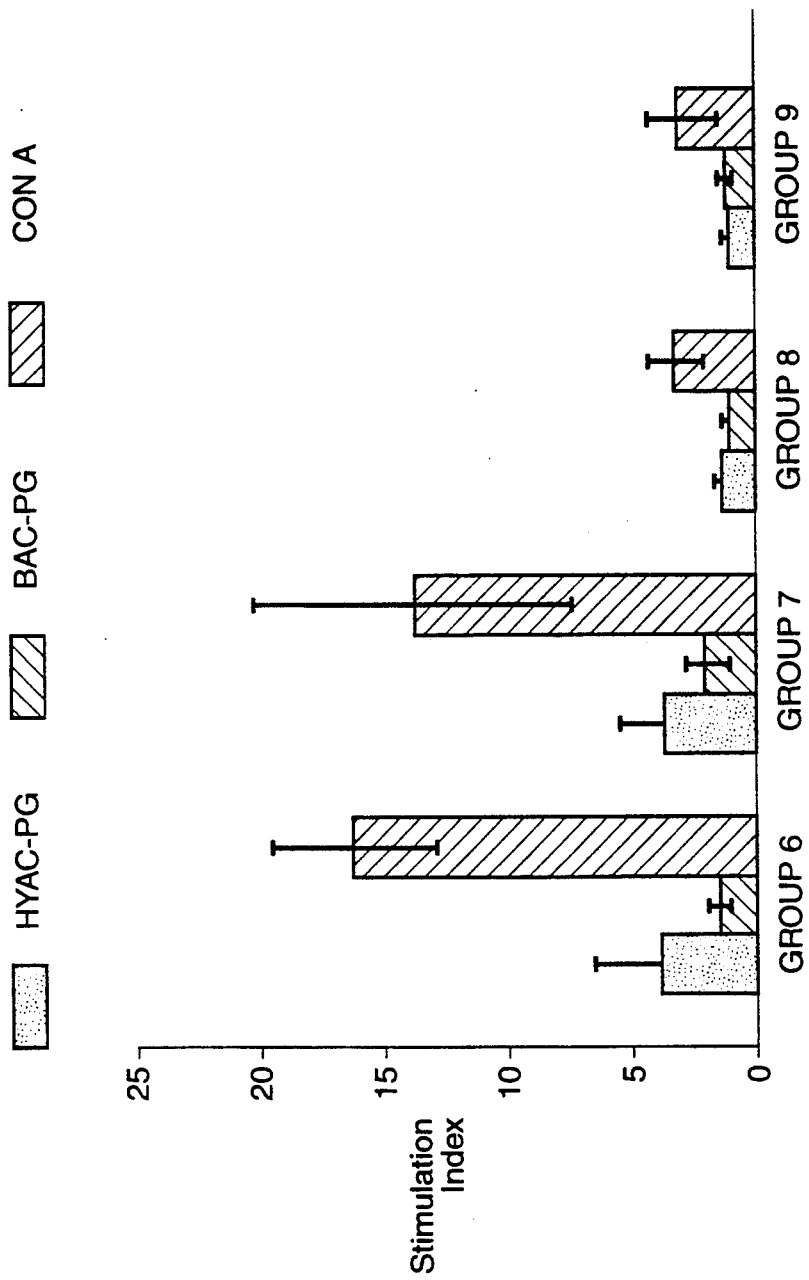
FIG. 11 a representation analogous to FIG. 7 of mice of the groups 6-9.

The level of circulating antibodies against proteoglycans of HYAC and mouse cartilage was suppressed from the second week of treatment but it started to increase after a short period of time even during the treatment with the higher (25 mg/kg/day) dose of ET-18-OCH$_3$ (FIG. 12). On the other hand, the antigen-stimulated and non-specific (Con A-induced) T-lymphocyte proliferation was equally suppressed in all treated animals (FIG. 11).

group 9 pretreated with ET-18-OCH$_3$ before immunisation with arthritogenic proteoglycan Animals (originally 10) of this group were treated orally with ET-18-OCH$_3$ 2 weeks before the first injection of the antigen. Unfortunately, 4 animals of this pretreated group died within the first 6 weeks of the experiment, which indicated that the 25 mg/kg/day dose of ET-18-OCH$_3$ is probably too high a dose for Balb/c mice. However, for reasons of comparison, the ET-18-OCH$_3$ dose was not reduced until two animals died in group 8 (see above).

The clinical parameters and physical condition of the animals were the same as in group 8 except that these pretreated animals did not show any clinical symptoms of arthritis. The lymphocyte stimulation with proteoglycans of bovine or human cartilages, as well as with Con A, was the same as in the case of animals of group 8 (i.e. there was a strong suppression not only of the specific but also of the non-specific T-lymphocyte response). Furthermore, the production of antibodies against cartilage proteoglycans was significantly delayed and antibodies were detected in the sera usually only after the fourth antigen injection.

CONCLUSION

The treatment of the Balb/c mice with ET-18-OCH$_3$ is able to suppress acute inflammatory events and blocks the progression of chronic arthritis in the cause of proteoglycan-induced arthritis. Furthermore, a pretreatment of animals with ET-18-OCH$_3$ seems to protect Balb/c mice from the appearance of inflammations, probably due to the suppression of a T-cell mediated immune response. The production of (auto)-antibodies was significantly suppressed during the treatment which were determined as antibody titres against human and mouse cartilage proteoglycans. This suppressive effect was probably constant for 3 to 4 weeks of the antibody production after oral administration of ET-18-OCH$_3$ and is then again removed by an unknown mechanism.

We claim:

1. Method for treating a subject with an autoimmune disease selected from he group consisting of rheumatoid arthritis and ankylosing spondylitis comprising administering to said subject with rheumatoid arthritis or ankylosing spondylitis an effective amount of a compound of formula

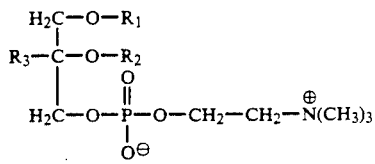

wherein R$_1$ is alkyl having from 12 to 18 carbon atoms, R$_2$ is alkyl having from 1 to 8 carbon atoms, and R$_3$ is H or alkyl having from 1 to 3 carbon atoms.

2. Method of claim 1, wherein said compound is:

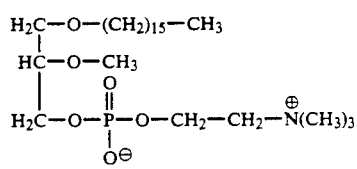

3. Method of claim 1, wherein said compound is

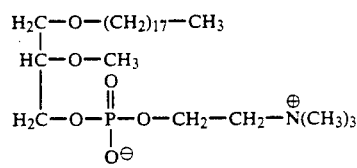

4. Method of claim 1, wherein said compound is administered at a dose of at least 20 mg/kg of body weight per day.

5. Method of claim 4, wherein said compound is administered at a dose of at least 25 mg/kg of body weight per day.

6. Method of claim 1, wherein said compound is administered orally.

7. Method of claim 6, wherein said compound is administered in a liquid.

* * * * *